US009811818B1

(12) United States Patent
Xing

(10) Patent No.: US 9,811,818 B1
(45) Date of Patent: Nov. 7, 2017

(54) WEARABLE PERSONAL DIGITAL DEVICE FOR FACILITATING MOBILE DEVICE PAYMENTS AND PERSONAL USE

(71) Applicants: WORLD AWARD ACADEMY, Austin, TX (US); WORLD AWARD FOUNDATION, Austin, TX (US); AMOBILEPAY, INC., Austin, TX (US)

(72) Inventor: Zhou Tian Xing, Tiburon, CA (US)

(73) Assignee: WORLD AWARD ACADEMY, WORLD AWARD FOUNDATION, AMOBILEPAY, INC., Austin, TX (US)

( * ) Notice: Subject to any disclaimer, the term of this patent is extended or adjusted under 35 U.S.C. 154(b) by 0 days.

(21) Appl. No.: 15/599,467

(22) Filed: May 19, 2017

Related U.S. Application Data

(63) Continuation-in-part of application No. 15/439,276, filed on Feb. 22, 2017, now Pat. No. 9,704,154, and
(Continued)

(51) Int. Cl.
*G06Q 20/32* (2012.01)
*A61B 5/00* (2006.01)
(Continued)

(52) U.S. Cl.
CPC .......... *G06Q 20/32* (2013.01); *G06K 15/00* (2013.01); *G06Q 20/00* (2013.01); *G06Q 20/02* (2013.01);
(Continued)

(58) Field of Classification Search
CPC .............. G06Q 20/32; G06Q 20/3276; G06Q 20/3274; G06Q 20/325; G06Q 20/00; G06Q 20/02; G06Q 20/16; G06Q 20/223; H04M 15/00; H04M 1/2755; H04M 1/725; G06K 19/06112; A61B 5/681; A61B 5/0024; A61B 5/1117; A61B 10/0051
See application file for complete search history.

(56) References Cited

U.S. PATENT DOCUMENTS

| 8,784,271 | B2 * | 7/2014 | Brumback | ........... | A61B 5/0015 |
| | | | | | 340/870.16 |
| 9,100,493 | B1 * | 8/2015 | Zhou | ................. | H04M 1/72522 |

(Continued)

*Primary Examiner* — Daniel Walsh
(74) *Attorney, Agent, or Firm* — Georgiy L. Khayet

(57) ABSTRACT

Provided is a wearable personal digital device for point of healthcare saliva testing. The wearable personal digital device may comprise a processor, a display, biometric sensors, activity tracking sensors, a memory unit, a communication circuit, a housing, an input unit, a projector, a timepiece unit, a haptic touch control actuator, a band, a mounting clip, a saliva sample insert apparatus, a pinhole, a light emitting diode board, a battery, and a set of sensors. The processor may be operable to receive data from an external device, provide a notification to a user based on the data, receive a user input, and perform a command selected based on the user input. The housing may be adapted to enclose the components of the wearable personal digital device. The band may be adapted to attach to the housing and secure the wearable personal digital device on a user body.

27 Claims, 16 Drawing Sheets

Related U.S. Application Data a continuation-in-part of application No. 14/695,256, filed on Apr. 24, 2015, now Pat. No. 9,100,493, and a continuation-in-part of application No. 15/343,227, filed on Nov. 4, 2016, now Pat. No. 9,704,151, said application No. 15/439,276 is a continuation of application No. 15/345,349, filed on Nov. 7, 2016, now Pat. No. 9,652,758, which is a continuation-in-part of application No. 14/957,644, filed on Dec. 3, 2015, now Pat. No. 9,489,671, which is a continuation-in-part of application No. 14/815,988, filed on Aug. 1, 2015, now Pat. No. 9,342,829, which is a continuation-in-part of application No. 13/760,214, filed on Feb. 6, 2013, now Pat. No. 9,016,565, which is a continuation-in-part of application No. 10/677,098, filed on Sep. 30, 2003, now Pat. No. 7,702,739.

(60) Provisional application No. 60/415,546, filed on Oct. 1, 2002.

(51) Int. Cl.

| | | |
|---|---|---|
| G06F 21/32 | (2013.01) | |
| H04M 15/00 | (2006.01) | |
| H04M 1/2755 | (2006.01) | |
| G06Q 20/00 | (2012.01) | |
| G06Q 20/02 | (2012.01) | |
| G06K 15/00 | (2006.01) | |
| H04M 1/725 | (2006.01) | |
| G06Q 20/16 | (2012.01) | |
| G06Q 20/22 | (2012.01) | |

(52) U.S. Cl.
CPC .......... G06Q 20/16 (2013.01); G06Q 20/223 (2013.01); G06Q 20/325 (2013.01); G06Q 20/3274 (2013.01); G06Q 20/3276 (2013.01); H04M 1/2755 (2013.01); H04M 1/725 (2013.01); H04M 15/00 (2013.01)

(56) References Cited

U.S. PATENT DOCUMENTS

| | | | | |
|---|---|---|---|---|
| 9,299,238 B1* | 3/2016 | Ahmad | ............... | A61B 5/4833 |
| 9,704,154 B2* | 7/2017 | Xing | ............... | G06Q 20/3278 |
| 2002/0055117 A1* | 5/2002 | Fett | ............... | C12Q 1/6886 |
| | | | | 435/6.14 |
| 2002/0059030 A1* | 5/2002 | Otworth | ............... | A61B 5/411 |
| | | | | 702/19 |
| 2003/0165954 A1* | 9/2003 | Katagiri | ............... | C12Q 1/6883 |
| | | | | 435/6.14 |
| 2003/0175993 A1* | 9/2003 | Toranto | ............... | G01N 33/487 |
| | | | | 436/518 |
| 2006/0018800 A1* | 1/2006 | Slowey | ............... | A61B 10/02 |
| | | | | 422/412 |
| 2006/0057707 A1* | 3/2006 | Cunningham | ........ | B01L 3/5085 |
| | | | | 435/287.1 |
| 2007/0031283 A1* | 2/2007 | Davis | ............... | A61B 5/14546 |
| | | | | 422/400 |
| 2008/0022089 A1* | 1/2008 | Leedom | ............... | H04L 63/068 |
| | | | | 713/156 |
| 2008/0038738 A1* | 2/2008 | Weigum | ............... | A61B 5/0059 |
| | | | | 435/6.12 |
| 2008/0266546 A1* | 10/2008 | Kolesnychenko | . | G01N 21/0303 |
| | | | | 356/51 |
| 2009/0120446 A1* | 5/2009 | Vaska | ............... | A61F 5/566 |
| | | | | 128/848 |
| 2009/0278659 A1* | 11/2009 | Barzaga Castellanos | .......... | C12Q 1/6813 |
| | | | | 340/5.82 |
| 2011/0153362 A1* | 6/2011 | Valin | ............... | G06Q 20/105 |
| | | | | 705/3 |
| 2013/0146659 A1* | 6/2013 | Zhou | ............... | G06Q 20/355 |
| | | | | 235/380 |
| 2013/0231711 A1* | 9/2013 | Kaib | ............... | G06F 19/3418 |
| | | | | 607/5 |
| 2013/0234850 A1* | 9/2013 | Lee | ............... | A61B 5/02 |
| | | | | 340/539.12 |
| 2013/0346168 A1* | 12/2013 | Zhou | ............... | G06F 1/163 |
| | | | | 705/14.4 |
| 2014/0139422 A1* | 5/2014 | Mistry | ............... | G06F 3/014 |
| | | | | 345/156 |
| 2014/0139486 A1* | 5/2014 | Mistry | ............... | G06F 3/0304 |
| | | | | 345/175 |
| 2014/0139637 A1* | 5/2014 | Mistry | ............... | H04N 5/2252 |
| | | | | 348/46 |
| 2014/0143737 A1* | 5/2014 | Mistry | ............... | G06F 3/0488 |
| | | | | 715/854 |
| 2014/0169795 A1* | 6/2014 | Clough | ............... | G06F 19/3418 |
| | | | | 398/106 |
| 2014/0180595 A1* | 6/2014 | Brumback | ............ | A61B 5/0015 |
| | | | | 702/19 |
| 2014/0239065 A1* | 8/2014 | Zhou | ............... | G06F 1/163 |
| | | | | 235/380 |
| 2014/0275850 A1* | 9/2014 | Venkatraman | ....... | A61B 5/0002 |
| | | | | 600/301 |
| 2014/0275852 A1* | 9/2014 | Hong | ............... | A61B 5/02427 |
| | | | | 600/301 |
| 2014/0275854 A1* | 9/2014 | Venkatraman | ......... | A61B 5/721 |
| | | | | 600/301 |
| 2014/0276244 A1* | 9/2014 | Kamyar | ............... | A61B 5/1112 |
| | | | | 600/595 |
| 2014/0316305 A1* | 10/2014 | Venkatraman | ........ | A61B 5/1112 |
| | | | | 600/595 |
| 2014/0366123 A1* | 12/2014 | DiBona | ............... | G06F 21/60 |
| | | | | 726/16 |
| 2015/0073907 A1* | 3/2015 | Purves | ............... | G06Q 20/32 |
| | | | | 705/14.58 |
| 2015/0126873 A1* | 5/2015 | Connor | ............... | A61B 5/4866 |
| | | | | 600/475 |
| 2015/0186609 A1* | 7/2015 | Utter, II | ............... | A61B 5/0022 |
| | | | | 600/301 |
| 2015/0196200 A1* | 7/2015 | Fixler | ............... | A61B 5/02007 |
| | | | | 600/431 |
| 2015/0238150 A1* | 8/2015 | Subramaniam | .......... | H04Q 9/00 |
| | | | | 340/539.11 |
| 2015/0366518 A1* | 12/2015 | Sampson | ............ | A61B 5/7221 |
| | | | | 600/301 |
| 2015/0371215 A1* | 12/2015 | Zhou | ............... | G06Q 30/02 |
| | | | | 705/71 |
| 2016/0036811 A1* | 2/2016 | Shim | ............... | G06F 21/6245 |
| | | | | 726/7 |
| 2016/0037346 A1* | 2/2016 | Boettcher | ......... | H04M 1/72519 |
| | | | | 455/411 |
| 2016/0125600 A1* | 5/2016 | Lee | ............... | G01N 21/8483 |
| | | | | 382/128 |
| 2016/0162873 A1* | 6/2016 | Zhou | ............... | G06Q 20/3227 |
| | | | | 705/67 |
| 2016/0239624 A1* | 8/2016 | Short | ............... | G06F 19/18 |
| 2016/0286210 A1* | 9/2016 | Border | ............... | G02B 27/0176 |
| 2016/0328282 A1* | 11/2016 | Rogati | ............... | G06F 11/0772 |
| 2016/0374588 A1* | 12/2016 | Shariff | ............... | A61B 5/7475 |
| | | | | 600/547 |
| 2016/0379205 A1* | 12/2016 | Margadoudakis | ... | G06Q 20/327 |
| | | | | 705/71 |
| 2017/0007215 A1* | 1/2017 | Podoly | ............... | A61C 17/046 |
| 2017/0011210 A1* | 1/2017 | Cheong | ............... | H04W 12/06 |
| 2017/0011223 A1* | 1/2017 | Dang | ............... | G06F 21/606 |
| 2017/0018150 A1* | 1/2017 | Kim | ............... | G07C 9/00 |
| 2017/0031449 A1* | 2/2017 | Karsten | ............... | G06F 19/322 |
| 2017/0039358 A1* | 2/2017 | Yuen | ............... | G06F 3/017 |
| 2017/0071483 A1* | 3/2017 | Wang | ............... | A61B 5/14551 |
| 2017/0161720 A1* | 6/2017 | Xing | ............... | G06Q 20/3278 |

* cited by examiner

WEARABLE PERSONAL DIGITAL DEVICE FOR FACILITATING MOBILE DEVICE PAYMENTS AND PERSONAL USE

CROSS-REFERENCE TO RELATED APPLICATIONS

This application is a continuation-in-part of U.S. patent application Ser. No. 15/439,276, entitled "WEARABLE PERSONAL DIGITAL DEVICE FOR FACILITATING MOBILE DEVICE PAYMENTS AND PERSONAL USE", filed on Feb. 22, 2017, U.S. patent application Ser. No. 14/695,256, entitled "WEARABLE PERSONAL DIGITAL DEVICE FOR FACILITATING MOBILE DEVICE PAYMENTS AND PERSONAL USE", filed on Apr. 24, 2015, U.S. patent application Ser. No. 15/345,349, entitled "SYSTEMS AND METHODS FOR MESSAGING, CALLING, DIGITAL MULTIMEDIA CAPTURE AND PAYMENT TRANSACTIONS", filed on Nov. 7, 2016; U.S. patent application Ser. No. 15/343,227, entitled "SYSTEMS AND METHODS FOR MOBILE APPLICATION, WEARABLE APPLICATION, TRANSACTIONAL MESSAGING, CALLING, DIGITAL MULTIMEDIA CAPTURE AND PAYMENT TRANSACTIONS", filed on Nov. 4, 2016, which is a continuation-in-part of U.S. patent application Ser. No. 14/957,644, entitled "SYSTEMS AND METHODS FOR MOBILE APPLICATION, WEARABLE APPLICATION, TRANSACTIONAL MESSAGING, CALLING, DIGITAL MULTIMEDIA CAPTURE AND PAYMENT TRANSACTIONS", filed on Dec. 3, 2015, which is a continuation-in-part of U.S. patent application Ser. No. 14/815,988, entitled "SYSTEMS AND METHODS FOR MOBILE APPLICATION, WEARABLE APPLICATION, TRANSACTIONAL MESSAGING, CALLING, DIGITAL MULTIMEDIA CAPTURE AND PAYMENT TRANSACTIONS", filed on Aug. 1, 2015, which claims priority to U.S. patent application Ser. No. 13/760,214, entitled "WEARABLE PERSONAL DIGITAL DEVICE FOR FACILITATING MOBILE DEVICE PAYMENTS AND PERSONAL USE", filed on Feb. 6, 2013, which is a continuation-in-part of U.S. patent application Ser. No. 10/677,098, entitled "EFFICIENT TRANSACTIONAL MESSAGING BETWEEN LOOSELY COUPLED CLIENT AND SERVER OVER MULTIPLE INTERMITTENT NETWORKS WITH POLICY BASED ROUTING", filed on Sep. 30, 2003, which claims priority to Provisional Application No. 60/415,546, entitled "DATA PROCESSING SYSTEM", filed on Oct. 1, 2002, which are incorporated herein by reference in their entirety, which are incorporated herein by reference in its entirety.

FIELD

This application relates generally to personal mobile devices and, more specifically, to wearable personal digital devices for facilitating mobile device payments and personal use.

BACKGROUND

Mobile devices gain growing importance in daily activities of their users with more and more functions being performed by mobile devices. Some of such functions may include mobile communication, mobile payments, health monitoring, and so forth. In addition to that, carrying a mobile phone, a tablet personal computer, or a laptop may not always be comfortable, for example, during physical activity or leisure time. For such purposes, wearable mobile devices, e.g. wristwatch digital devices, may be used. However, use of the wearable mobile devices may be inconvenient because of limited software functionality of such devices.

Furthermore, a wristwatch digital device may be communicatively coupled to a smartphone and display notifications related to smartphone activity, e.g. an incoming call or a message. However, a user may be unable to respond to the notification directly using the wristwatch digital device. Additionally, conventional mobile devices cannot be used for personal saliva testing, personal urine testing, or personal blood testing.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Provided are Artificial Intelligence (AI) wearable and mobile personal digital devices for facilitating mobile device payments, personal saliva testing, personal use, and health care being point of healthcare (POH) saliva testing devices for POH saliva testing. An AI wearable and mobile personal digital device may include a mounting clip, a saliva sample insert apparatus, a pinhole, a light-emitting diode (LED) board, a battery, a set of sensors, and a processor. The processor may be operable to receive data from an external device associated with POH saliva testing. Based on the data, the processor may provide a notification to a user. The processor may be further configured to receive a user input and perform a command, which may be selected based on the user input. The processor may be further operable to provide a natural language user interface to communicate with the user. The natural language user interface may be operable to sense a user voice and provide a response in a natural language to the user. The AI wearable and mobile personal digital device may include a near field communication (NFC) unit communicatively coupled to the processor and a display communicatively coupled to the processor. The display may include a touchscreen. The display may further include a force sensor operable to sense a touch force applied by the user to the display and calculate coordinates of a touch by the user, and further operable to analyze the touch force and, based on the touch force, select a tap command or a press command based on a predetermined criteria.

The AI wearable and mobile personal digital device may include a projector communicatively coupled to the processor. The projector may be operable to project a data onto a viewing surface external to the AI wearable and mobile personal digital device. The data may include a virtual keyboard operable to input commands to the processor and one or more of the following: the notification of the external device, time, and data requested by the user, a caller name, a text message, a reminder, a social media alert, an email, a weather alert, and so forth.

The AI wearable and mobile personal digital device may include a timepiece unit communicatively coupled to the processor and configured to provide time data. The AI wearable and mobile personal digital device may further include one or more activity tracking sensors communicatively coupled to the processor to track activity of the user. The one or more activity tracking sensors may be operable to track snoring and, based on tracking of the snoring, produce an alarm to break snoring. The AI wearable and mobile personal digital device may further include a memory unit communicatively coupled to the processor, and a communication circuit communicatively coupled to the processor and operable to connect to a wireless network and communicate with the external device. The AI wearable and mobile personal digital device may include a housing adapted to enclose at least the processor, the display, the one or more activity tracking sensors, the memory unit, and the communication circuit.

The AI wearable and mobile personal digital device may further include an input unit communicatively coupled to the processor. The input unit may extend from the housing and may be configured to perform one or more of a rotational motion and a linear motion. The one or more motions may be operable to input commands to the processor.

The AI wearable and mobile personal digital device may further include a band adapted to attach to the housing and to secure the AI wearable and mobile personal digital device on a user body. More specifically, the AI wearable and mobile personal digital device may include a wristwatch.

The AI wearable and mobile personal digital device may further include one or more biometric sensors disposed within the band and operable to sense one or more biometric parameters of the user. Based on detection that the one or more of the biometric parameters exceed predetermined limits, the one or more biometric sensors may be configured to produce the alarm. The one or more biometric sensors may include lenses operable to use infrared LEDs and visible-light LEDs to sense a heart rate of the user. The one or more biometric sensors may include a skin contact sensor data engine. The skin contact sensor data engine may be operable to monitor an electrocardiogram of the user and the heart rate of the user. The electrocardiogram and the heart rate may be identification and personal data of the user. The skin contact sensor data engine may be operable to prompt the user to enter a personal identification number and associate the personal identification number with both the electrocardiogram and the heart rate obtained after the AI wearable and mobile personal device has been secured to a wrist of the user. The electrocardiogram and the heart rate may be stored in the memory unit as a reference electrocardiogram and a reference heart rate.

Additionally, a thermal infrared (IR) measurement of the one or more biometric sensors may be used to investigate a potential of cancer detection. The one or more biometric sensors may include an adhesive sensor system worn on the skin that automatically detects human falls and fatal diseases, a sensor consisting of a tri-axial accelerometer, a microcontroller, and a Bluetooth Low Energy transceiver and worn on the user body to detect a biological analyte by converting a biological entity into an electrical signal to be detected and analyzed by using a biosensor in cancer and fatal diseases detection and monitoring.

The AI wearable and mobile personal digital device may further include a haptic touch control actuator operable to produce a haptic feedback in response to one or more events. The one or more events may include receiving of the alert, receiving of a notification, a confirmation, movement of the AI wearable and mobile personal digital device, receiving of the user input, and sensing of the one or more biometric parameters. The haptic feedback may be sensed by the user body. The haptic feedback may include a plurality of feedback types. Each of the one or more events may be associated with one of the plurality of feedback types. The user input may be received using one or more of the display, the input unit, and the natural language user interface.

The AI wearable and mobile personal digital device may further include a battery disposed in the housing and a magnetic inductive charging unit operable to magnetically connect to the housing and wirelessly connect to the battery. The magnetic inductive charging unit may be operable to wirelessly transfer energy to the battery. The magnetic inductive charging unit may be integrated into the housing.

The AI wearable and mobile personal digital device may further include a camera communicatively coupled to the processor and operable to capture a code. The code may include one or more of the following: a linear dimensional barcode, a two-dimensional barcode, a snap tag code, and a Quick Response (QR) code. The processor may be further operable to read the code to obtain one or more of a product information and a merchant information encoded in the code and, based on the merchant information, initiate a payment transaction. The payment transaction may be performed by sending payment data by the NFC unit to a merchant using the NFC.

The AI wearable and mobile personal digital device may further include a swipe card reader communicatively coupled to the processor and operable to read data of a payment card swiped through the swipe card reader. The data may be transmitted to the processor or the external device.

The processor may be further operable to generate, based on user payment data and user personal data, a unique code encoding the user payment data and the user personal data. The user payment data and the user personal data may be stored in the memory unit. The processor may be further operable to prompt the user to touch the display to scan user fingerprints, determine the heart rate and the electrocardiogram of the user to obtain determined heart rate and determined electrocardiogram, and compare the scanned user fingerprints, the heart rate and the user electrocardiogram with reference fingerprints stored in the memory unit, the reference heart rate, and the reference electrocardiogram. The processor may be further operable to detect matches of the scanned user fingerprints with the reference fingerprints, the determined heart rate with the reference heart rate, and the determined electrocardiogram with the reference electrocardiogram. After the detecting of the matches, the processor may provide the unique code via the display to a merchant digital device associated with one or more of a healthcare center, a hospital, an emergency center, and a saliva research center for performing the payment transaction. Upon performing the payment transaction, the processor may provide a payment confirmation to the user.

In further exemplary embodiments, modules, subsystems, or devices can be adapted to perform the recited steps. Other features and exemplary embodiments are described below.

BRIEF DESCRIPTION OF DRAWINGS

Embodiments are illustrated by way of example and not limitation in the figures of the accompanying drawings, in which like references indicate similar elements and in which.

DETAILED DESCRIPTION

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting.

A wearable personal digital (WPD) device for facilitating mobile device payments, personal use, and health care and related methods are described herein. The WPD device may include a housing enclosing all components of the WPD device and a band attached to the housing. Furthermore, the WPD device may perform a function of a health and activity monitor. More specifically, the WPD device may sense biometric data associated with the user (blood pressure, heart rate, temperature, and so forth) using biometric sensors and/or receive data on user movements using accelerometers or a Global Positioning System (GPS) unit. Biometric data and user movement data may be shown on a display of the WPD device, stored in a memory unit of the WPD device, and/or processed by a processor of the WPD device to produce historical or averaged data.

The WPD device may be communicatively coupled with an external device, such as a smartphone. The WPD device and the smartphone may communicate using a wireless network, such as a Wi-Fi network or a Bluetooth network. The WPD device may display notifications from the smartphone. The notifications may represent receipt of any type of data by the smartphone, for example, a phone call, a message, an upcoming calendar event, a social network event, and the like. A user may respond to the notification directly via the WPD device, or using the smartphone. The biometric data and user movement data collected by the WPD device may be sent to the smartphone for further processing.

The display of the WPD device may be represented by a touchscreen. The user may provide commands to the WPD device by varying the time of user interaction with the touchscreen. More specifically, the user may vary the time of pressing the touchscreen. Different time of pressing the touchscreen may correspond to different commands. For example, pressing the touchscreen for 1 second may correspond to a message mode. Therefore, after the user touches the touchscreen for 1 sec and releases a user finger from the touchscreen, the message mode may be activated. Similarly, pressing the touchscreen for 5 seconds may correspond to a payment mode. The payment mode may be performed by using scanning of codes. Additionally, payment cards may be read using a swipe card reader optionally included into the WPD device.

Figure 1:
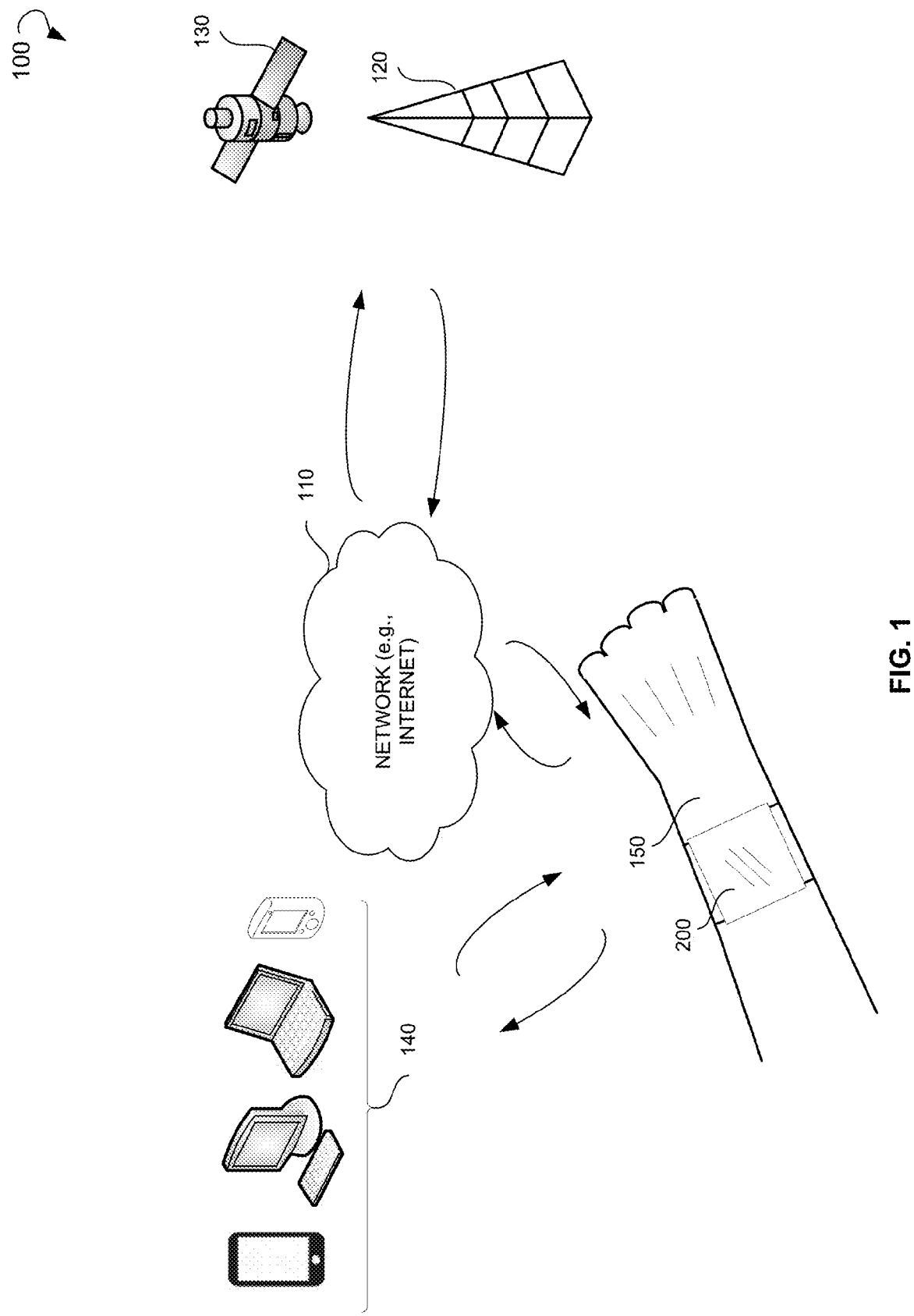
FIG. 1 illustrates an environment within which the wearable personal digital device for facilitating mobile device payments, personal use, and health care and methods for facilitating user interaction with the wearable personal digital device for facilitating mobile device payments and personal use can be implemented, in accordance with some embodiments.

Referring now to the drawings, FIG. 1 illustrates an environment 100 within which the WPD device 200 and methods for facilitating user interaction with the WPD device 200 can be implemented. The environment 100 may include a network 110, a WPD device 200, a mobile base station 120, a GSM satellite 130, and one or more external devices 140. The WPD device 200 may be worn by a user 150. The network 110 may include the Internet or any other network capable of communicating data between devices. Suitable networks may include or interface with any one or more of, for instance, a Personal Area Network, a Local Area Network, a Wide Area Network, a Metropolitan Area Network, a virtual private network, a storage area network, a frame relay connection, an Advanced Intelligent Network connection, a synchronous optical network connection, a digital T1, T3, E1 or E3 line, Digital Data Service connection, Digital Subscriber Line connection, an Ethernet connection, an Integrated Services Digital Network line, a dial-up port such as a V.90, V.34 or V.34bis analog modem connection, a cable modem, an Asynchronous Transfer Mode connection, or an Fiber Distributed Data Interface or Copper Distributed Data Interface connection. Furthermore, communications may also include links to any of a variety of wireless networks, including Wireless Application Protocol, General Packet Radio Service, Global System for Mobile Communication, Code Division Multiple Access or Time Division Multiple Access, cellular phone networks, Global Positioning System, cellular digital packet data, Research in Motion, Limited duplex paging network, Bluetooth radio, or an IEEE 802.11-based radio frequency network. The network 110 can further include or interface with any one or more of an RS-232 serial connection, an IEEE-1394 (Firewire) connection, a Fiber Channel connection, an IrDA (infrared) port, a SCSI (Small Computer Systems Interface) connection, a Universal Serial Bus (USB) connection or other wired or wireless, digital or analog interface or connection, mesh or Digi® networking. The network 110 may be a network of data processing nodes that are interconnected for the purpose of data communication. The WPD device 200 may communicate with the GPS satellite via the network 110 to exchange data on a geographical location of the WPD device 200. Additionally, the WPD device 200 may communicate with mobile network operators using the mobile base station 120.

For the purposes of communication, the WPD device 200 may be compatible with one or more of the following network standards: GSM, CDMA, LTE, IMS, Universal Mobile Telecommunication System (UMTS), 4G, 5G, 6G and upper, RFID, and so forth.

Figure 2:
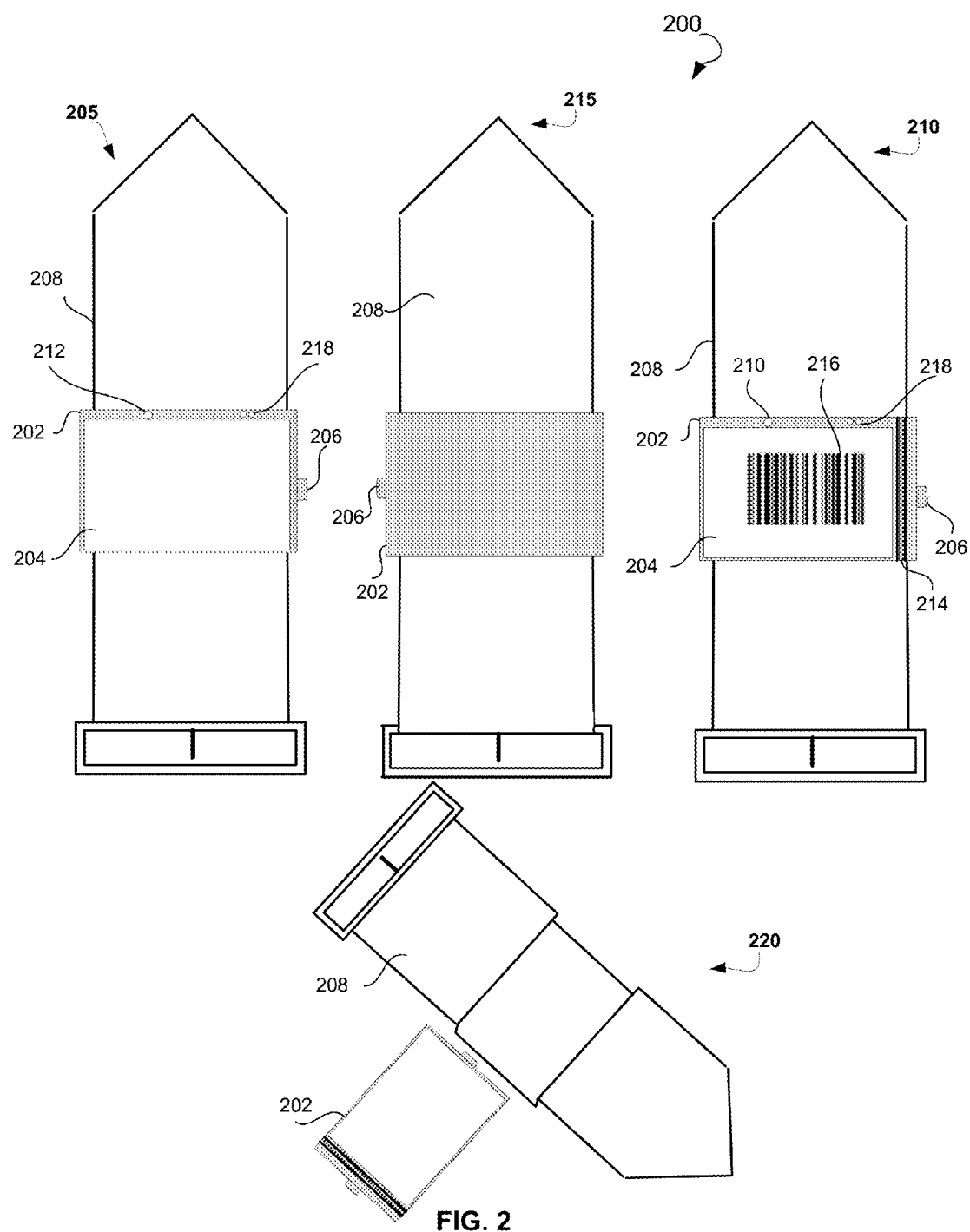
FIG. 2 illustrates an example wearable personal digital device for facilitating mobile device payments, personal use, and health care, in accordance with some embodiments.

FIG. 2 illustrates an example of the WPD device 200 in accordance with some embodiments. FIG. 2 shows a front view 205 of the WPD device 200 according to one example embodiment, a front view 210 of the WPD device 200 according to another example embodiment, a back view 215 of the WPD device 200 according to an example embodiment, and a detached view 220 of the WPD device 200 according to an example embodiment.

As shown on the front view 205 and the back view 215 of FIG. 2, the WPD device 200 may comprise a housing 202, which encloses a processor (not shown), a display 204, a memory unit (not shown) communicatively coupled to the processor, a communication circuit (not shown), biometric sensors (not shown) operable to sense one or more biometric parameters of the user, activity tracking sensors (not shown), an input unit 206, a projector (not shown), a timepiece unit (not shown), a haptic touch control actuator (not shown), an NFC unit (not shown) communicatively coupled to the processor, and a band 208.

The processor may be operable to receive data from an external device (not shown). Based on the data, the processor may be operable to provide a notification to a user. In an example embodiment, the notification may be provided via one or more of the following: a vibration, a sound, a light indication, and so forth. The light indication may be generated using a light indicator 218. The processor may be further operable to receive a user input provided by the user in response to reviewing the notification. Furthermore, the processor may be operable to perform a command selected based on the user input. The processor may be further operable to provide a natural language user interface to communicate with the user. The natural language user interface may be operable to sense a user voice and provide a response in a natural language to the user. The WPD device 200 may further include an operating system being executed on the processor. The operating system may include Android, iOS, Firefox OS, and so forth.

The display 204 may be communicatively coupled to the processor. In an example embodiment, the display 204 includes a touchscreen. The display 204 may be used to receive the user input. More specifically, the user may provide the user input by pressing the display 204, performing movements on the display 204 (e.g. moving a finger from left to right, from up to down, and the like). In an example embodiment, the display 204 includes a force sensor. The force sensor may be operable to sense a touch force applied by the user to the display 204 and calculate coordinates of a touch by the user. The force sensor may be further operable to analyze the touch force and, based on the touch force, select a tap command or a press command based on a predetermined criteria. The predetermined criteria may include a value of the touch force. In an example embodiment, the display 204 may be operable to be activated based on one or more of the following: a movement of a user hand, a movement of the user body, a gesture performed by the user in proximity to the display, a user voice, and so forth.

In a further example embodiment, the processor may be operable to detect absence of interaction of the user with the display. The detection may be made based on an eye tracking of the user, a head tracking of the user, and a spatial position of the housing. Based on the detecting, the processor may be operable to dim the display 204. Additionally, the processor may be operable to activate the display 204 based on a spatial position of the housing or a gesture of the user body, such as a user hand.

In a further example embodiment, the processor may be operable to receive, using the natural language user interface, a map request from the user. In response to the map request, the processor may display via the display 204, a map and a route depicted on the map. Additionally, the processor may be operable to provide an indication associated with the route to the user. The indication may be provided using the haptic feedback. The indication may include for example, providing haptic feedback, such as a vibration, one time for a direction to the left, two times for the direction to the right, or any other type of feedback.

In a further example embodiment, the processor may be operable to analyze a message received by the external device. The analyzing may include one or more of the following: parsing a text; reading an image, recognizing a voice, and the like. Based on the analysis, one or more possible replies may be displayed to the user using the display 204. Furthermore, a selection of a reply from the one or more possible replies may be received from the user. Based on the selection, the processor may be operable to send the reply to the external device.

In an example embodiment, the processor may be operable to analyze the user activity. Based on the analyzing, one or more diagrams may be displayed to the user. The one or mode diagrams may represent one or more activity types of the user.

The projector may be communicatively coupled to the processor. The projector may be operable to project a data onto a viewing surface. The data may include one or more of the following: a virtual keyboard, the notification of the external device, time, data requested by the user, a caller name, a text message, a reminder, a social media alert, an email, a weather alert, and the like. The viewing surface may include a user arm, a user hand, and any surface in proximity to the WPD device 200. In an example embodiment, the projector may project data to the left side or to the right side with respect to the wrist of the user.

The timepiece unit may be communicatively coupled to the processor and configured to provide time data.

The communication circuit may be communicatively coupled to the processor and configured to connect to a wireless network and communicate with the external device. In an example embodiment, the communication circuit may include one or more of the following: a wireless transceiver, a Bluetooth module, a Wi-Fi module, a communication port, and the like. The communication port may include one or more of the following: a USB port, a parallel port, an infrared transceiver port, a radiofrequency transceiver port, and so forth.

The input unit 206 may be communicatively coupled to the processor. In an example embodiment, the input unit 206 may extend from the housing 202 and may be configured to perform a rotational motion and a linear motion. Therefore, the input unit 206 may be rotated around a longitudinal axis of the input unit 206, may be pushed into the housing 202, or may be extended from the housing 202. Thus, the input unit 206 may be operable to receive the user input.

The band 208 may be adapted to attach to the housing 202 and to secure the WPD device 200 on a user body or clothes of the user. In various embodiments, the WPD device 200 may be secured on a wrist, an arm, a neck, a head, a leg, a waist, an ear, a finger, or any other part of the human body, or on any part of the clothes of the user. The band 208 may be adapted to secure the WPD device 200 under, within or on the clothes of the user. The band 208 may be an expansion bracelet, one piece band, two piece band, and so forth. In some embodiments, the band 208 may include a clasp adapted to fix the band 208 in a specific position to secure the WPD device 200 around the wrist.

In an example embodiment, the WPD device 200 may further include a camera 212. The camera 212 may be configured to capture a code, such as a linear dimensional code, a two-dimensional code, a snap tag code, and a Quick Response (QR) code. Upon capturing the code by the camera 212, the processor may be operable to read the captured code to obtain product information or merchant information encoded in the code. More specifically, the user may capture barcodes of products provided in a store. Upon reading the barcode, product information may be provided to the user on the display 204. In an example embodiment, the product information may be displayed on the external device, such as a smartphone. Additionally, the merchant information may be retrieved from the barcode. The merchant information may include merchant payment information. Upon obtaining product information and merchant information, the processor may initiate a payment transaction based on the merchant information. During the payment transaction, an amount of money corresponding to a price of the product may be transferred from a user payment account to a merchant payment account. The price of the product may be included into the product information. The payment transaction may be performed by sending payment data by a NFC unit of the WPD device to a merchant using a NFC.

In an example embodiment, the NFC may be used for payments for purchases made online and offline. A user of the WPD device 200 equipped with the NFC unit may perform transactions without authentication, or some authentication may be needed, such as a Personal Identification Number (PIN), before transaction is completed. The payment can be deducted from a pre-paid account of the user or charged directly to a bank account of the user. In example embodiment, the NFC unit may enable the WPD device 200 to establish radio communication with external devices by touching the WPD device 200 and the external device together or bringing them into proximity.

In an example embodiment, the camera 212 may be further operable to track a face, fingers, gestures, and other biometric personal data of the user. In turn, the processor may be operable to analyze the face, the fingers, the gestures, and the other biometric personal data tracked by the camera. Additionally, the processor may recognize speech and subtract a background noise from the speech.

The camera 212 may be further operable to perform an optical character recognition of a data. The data may include one or more of the following: a typewritten text, a printed text, an image, and the like. The data may be scanned from a document, such as a passport, an invoice, a bank statement, a computerized receipt, a business card, a mail, a printout of static-data, a book, a print publication, and so forth.

Figure 3:
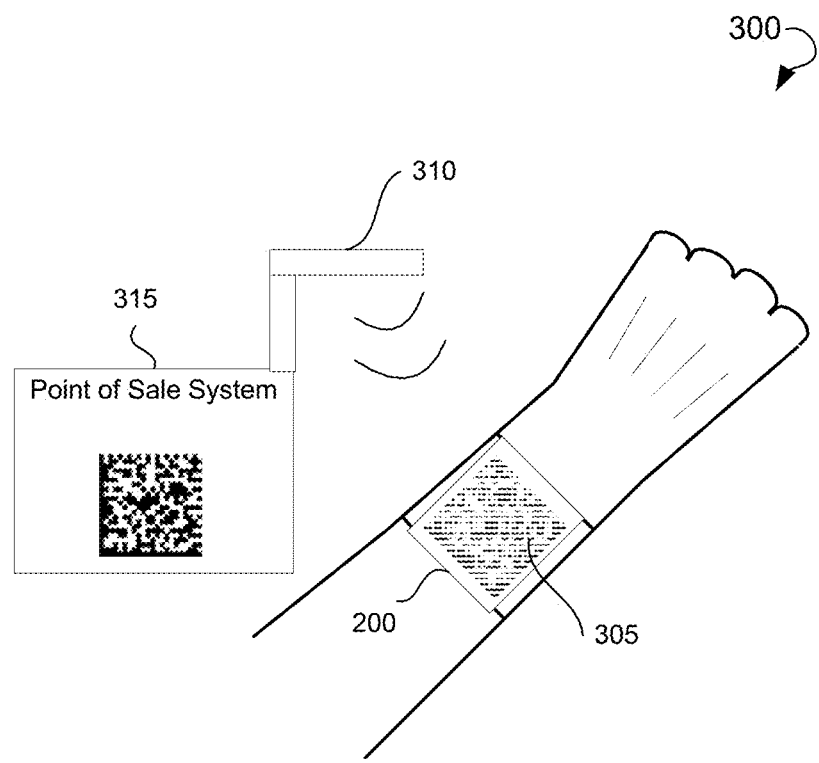
FIG. 3 illustrates an example of a wearable personal digital device for facilitating mobile device payments, personal use, and health care scannable by a Point-of-Sale system, in accordance with some embodiments.

In a further example embodiment, the WPD device 200 may be adapted to display a unique code to be scanned by a Point-of-Sale (POS) system. FIG. 3 shows a schematic representation 300 of scanning a barcode 305 displayed on the WPD device 200 by a barcode scanner 310 of the POS system 315. The barcode 305 may encode user payment information, such as a bank account, a payment card number, and so forth. The barcode 305 may be generated by a payment system (not shown) associated with the WPD device 200 or the external device. Therefore, the user may use the barcode 305 instead of a debit card or a credit card.

Referring back to FIG. 2, the front view 210 of the WPD device 200 shows an example embodiment, according to which the WPD device 200 includes a swipe card reader 214 communicatively coupled to the processor. The swipe card reader 214 may be located on either side of the WPD device 200, vertically or horizontally. The swipe card reader 214 may be operable to read data of a payment card. Upon reading, the data may be transmitted to the processor of the WPD device 200 or to the external device. The swipe card reader 214 may be used, for example, during performing payments on-line. Furthermore, the swipe card reader 214 may be used for providing user payment information, which may be further encoded into a barcode 216. The barcode 216 may be displayed on the display 204, e.g., in a store, for performing the payment transaction.

The biometric parameters sensed by the biometric sensors may be stored to the memory unit of the WPD device 200. According to another embodiment, the biometric parameters sensed by the biometric sensors may be transmitted to the external device for further processing or displaying on the external device. The processor may be operable to provide data associated with biometric parameters to be displayed on the display 204. The biometric parameters may include one or more of the following: a blood pressure, a heart rate, a glucose level, a body temperature, an environment temperature, arterial properties of the user, and the like. The biometric sensors may be disposed within the band. Based on detection that the one or more of the biometric parameters of the user exceed predetermined limits, the biometric sensors may be configured to produce the alarm. In an example embodiment, the biometric sensors include lenses operable to use infrared light-emitting diodes (LED) and visible-light LEDs to sense a heart rate of the user. In a further example embodiment, the biometric sensors may be operable to non-invasively monitor a glucose level. The glucose level may be monitored using a saliva testing. Wearable device may be integrated with one or more thin film silicon photonic biosensor that uses beams of light to detect tiny changes in the composition of a saliva or urine sample on the screen of wearable device or mobile device, which essentially looks at the level of binding between a DNA probe and target microRNA to figure out the level of microRNA in the sample. This can then provide clues to the presence of some types of cancer, cardiac disease, and other serious health issues via artificial intelligence (AI) big data analysis.

The biometric sensors may further include a skin contact sensor data engine. The skin contact sensor data engine may be operable to monitor a user electrocardiogram or the heart rate. The user electrocardiogram and the heart rate may serve as identification and personal data of the user. The skin contact sensor data engine may be further operable to prompt the user to enter a PIN after placing the WPD device 200 on the wrist. The skin contact sensor data engine may associate the PIN with the user electrocardiogram and the heart rate. Therefore, in case of placing the WPD device 200 on a wrist of another user, another user may be not authorized to user the WPD device 200 because a user electrocardiogram and a heart rate of another user may differ from those of the user of the WPD device 200.

A thermal infrared (IR) measurement of sensor may be used to investigate the potential of cancer detection. An adhesive sensor system worn on the skin that may automatically detect human falls and fatal diseases, the sensor, which may consist of a tri-axial accelerometer, a microcontroller and a Bluetooth Low Energy transceiver, can be worn anywhere on a human body to detect a specific biological analyte by essentially converting a biological entity into an electrical signal that can be detected and analyzed by using of biosensor in cancer and other fatal diseases detection and monitoring.

The haptic touch control actuator may be operable to produce a haptic feedback in response to one or more events. The one or more events may include receiving of the alert, receiving a notification, a confirmation, movement of the WPD device 200, receiving of the user input, sensing of the one or more biometric parameters, and so forth. The haptic feedback may be sensed by the user body, such as a wrist of the user. The haptic feedback may have a plurality of feedback types. More specifically, each of the one or more events may be associated with one of the plurality of feedback types.

In a further example embodiment, the display 204 may be further operable to display data associated with the activity of the user. The activity of the user may include calories burned, sleep quality, breaths per minute, snoring breaks, steps walked, distance walked and the like. The activity of the user may be tracked by the activity tracking sensors of the WPD device 200. The activity tracking sensors may be operable to monitor user movements in a three-dimensional trajectory, identify type of user activity, identify a specific motion fingerprint of an exercise, evaluate user physical form, count repetitions, calculate calories burned, and so forth. In certain example embodiments, the activity tracking sensors may sense and track position of the user to identify the snoring of the user and provide a notification to the user, e.g. using the vibration, to force the user to change the position. In an example embodiment, the activity tracking sensors are operable to track snoring of the user and, based on tracking of the snoring, produce an alarm to the user to break snoring.

In an example embodiment, the WPD device 200 may further include a microphone (not shown). The microphone may be operable to sense voice data. The voice data may be obtained from the user. For example, the user may provide a user request using user voice. The voice data may include a voice command, a voice memo, a voice message, and the like. The voice data may be transmitted to the processor for further processing. In particular, the processor may be operable to recognize the voice data in order to obtain the user request. The user request may be transmitted to the external device.

In an example embodiment, the input unit 206 may include a clock crown located on any of lateral sides of the housing, an upper side of the housing, or a bottom side of the housing. The processor may be operable to sense the rotational motion of the input unit 206. For example, the user may rotate the input unit 206. Based on the sensing, the data displayed on the display 204 may be scrolled. Each action performed by the user on the input unit 206, such as direction of rotation (e.g., clockwise or counter clockwise), speed of rotation, pressing the input unit 206 towards the housing 202, or extending the input unit 206 outwards the housing 202, may correspond to a specific command.

In a further example embodiment, the processor of the WPD device 200 may be operable to control an operation of a camera of the external device. Furthermore, the processor may access audio files stored on the external device and wirelessly connect with earphones. Upon accessing the external device and connecting with the earphones, the processor may reproduce the audio files using the earphones. Therefore, the user of the WPD device 200 may listen to the music stored on the external device and control reproducing of the audio files using the WPD device 200.

In an example embodiment, the processor may be further operable to generate a code encoding user payment data and user personal data. The generation may be performed based on the user payment data and the user personal data stored in the memory unit of the WPD device 200. The processor may be further operable to prompt the user to touch the display to scan user fingerprints. Additionally, the processor may be further operable to determine a heart rate of the user using the biometric sensors. The processor may be further operable to compare the user fingerprints and the heart rate of the user with reference fingerprints and a reference heart rate. The reference fingerprints and the reference heart rate may be stored in the memory unit. The processor may detect a match of the user fingerprints with the reference fingerprints and of the heart rate of the user with the reference heart rate. Base of the detecting, the processor may provide the code to a merchant digital device for performing a payment transaction. Upon the payment transaction, a payment confirmation may be provided to the user. The payment confirmation may be provided using the haptic feedback.

In an example embodiment, the processor may be further operable to detect current user location, e.g. using a GPS unit. The processor may be operable to detect presence of premises associated with the user in proximity to the current user location. The premises may include a home, an office, a garage, a car, and the like. Based on the detecting, the processor may be operable to initiate unlocking of the premises.

In a further example embodiment, the processor of the WPD device 200 may be operable to detect presence of another WPD device in proximity to the WPD device 200.

Based on the detecting, the processor may be operable to initiate data transmission between the WPD device 200 and another WPD device.

In an example embodiment, the processor may be further operable to receive, from the user, a content access request for at least one content item of content data stored in the memory unit of the WPD device 200. The processor may read access rules stored in the memory unit. The access rules may be associated with use of the at least one content item. Based on the access rules, the processor may be operable to determine that an access to the at least one content item is permitted. Based on the determining, the at least one content item may be reproduced to the user.

The content data may include audio data, video data, text, software, and game data. The WPD device 200 may act as a data carrier and include an interface for sending and receiving data. The memory unit may be operable to store received content data, provide payment validation data to the external device, store a record of access made to the stored content data, and the access rules for controlling access to the stored content data. The processor may be further operable to access control data and supplementary data including hot links to websites and advertising data. Payment data, the stored content data and access rules data may be used to reduce a risk of an unauthorized access to the content data.

The WPD device 200 may further include a battery (not shown) disposed in the housing. Additionally, the WPD device 200 may include a magnetic inductive charging unit (not shown). The magnetic inductive charging unit may be operable to magnetically connect to the housing and wirelessly connect to the battery. The magnetic inductive charging unit may be operable to wirelessly transfer energy to the battery. In some example embodiments, the magnetic inductive charging unit may be integrated into the housing. Once connected magnetically to the back of the WPD device 200, the connection of magnetic inductive charging unit may be seamless and need no additional alignment by the user.

The WPD device 200 may further include a light indicator operable to show a light indication in response to receiving data from an external device. Upon a predetermined movement of the user body, such as raising a hand, the light indication may stop showing the light indication and initiate the display to display the data received from an external device.

In example embodiments, the housing may have round, square, rectangular and other shape. Therefore, when the WPD device 200 is paired with the external device, a plurality of applications running on the external device may be visualized on the display of the WPD device 200 using a form factor specific to the form and size of the housing.

Figure 4:
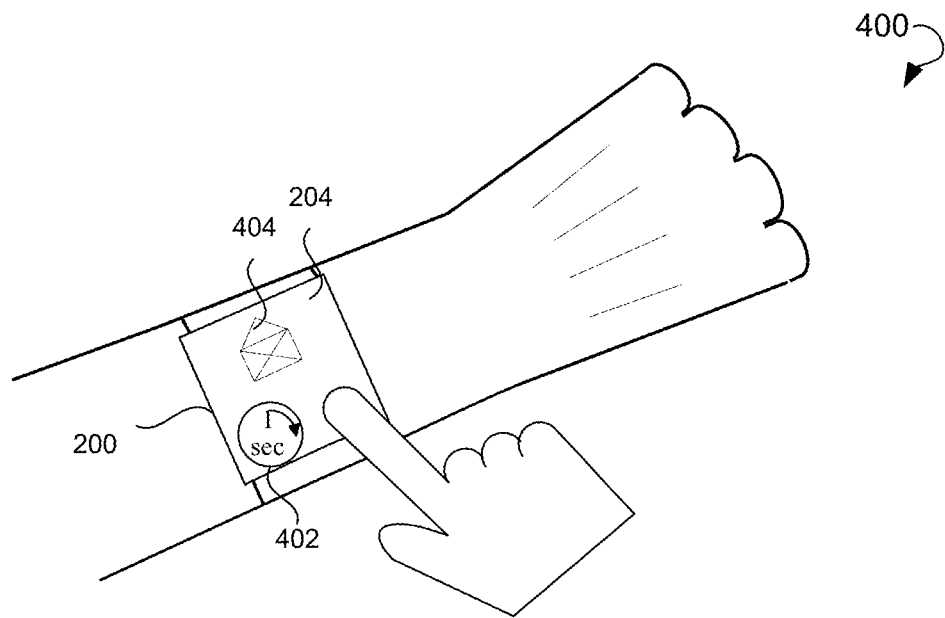
FIG. 4 shows user interaction with a display of a wearable personal digital device for facilitating mobile device payments, personal use, and health care, in accordance with some embodiments
Figure 4:
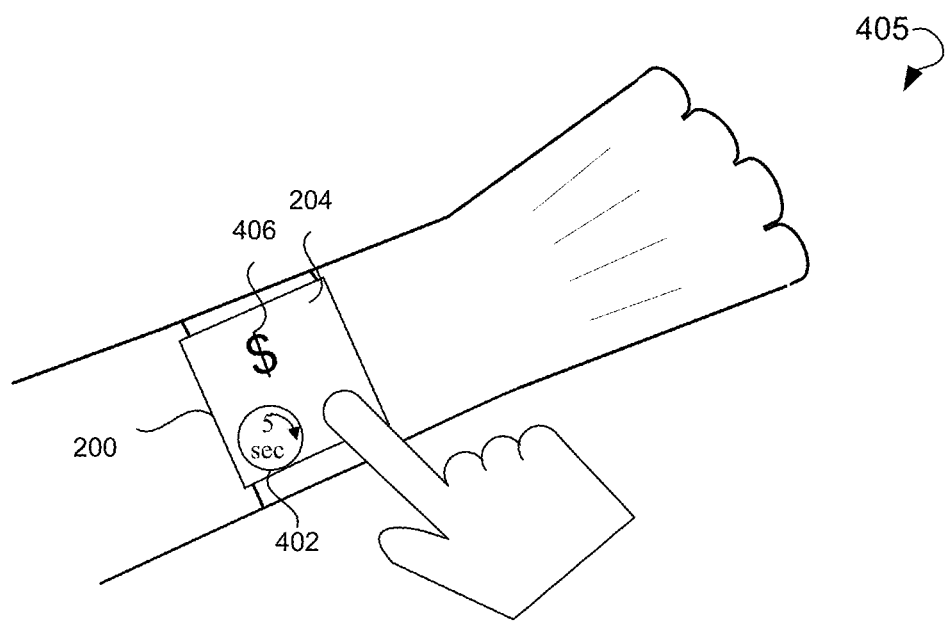

FIG. 4 shows diagrams 400 and 405 that represent user interaction with the display 204 of the WPD device 200. The user may provide the user input by pressing the display 204 for a predetermined time. The processor may estimate time of the user input. The time of user input may correspond to a specific command. The memory unit may store a table representing relationship between duration of pressing and a plurality of commands. For example, as shown on the diagram 400, the user may press the display 204 for 1 second. The time of 1 second may correspond to a message mode. Therefore, based on the time of 1 second, the processor may select a command from the table, such as initiation of the message mode. The processor may further perform the selected command, namely, initiate the message mode. During the time when the user presses the display 204, a timer 402 may be displayed on the display 204. The timer 402 may show the time the user presses the display 204. Additionally, an icon 404 may be displayed. The icon 404 may represent a command corresponding to the time currently shown on the timer 402. For example, the icon 404 may represent the message mode.

In another example embodiment, as shown on the diagram 405, the user may press the display 204 for 5 seconds. The time of 5 seconds may correspond to a payment mode. Therefore, based on the time of 5 second, the processor may select a command from the table, such as initiation of the payment mode. The timer 402 may show the time the user presses the display 204, namely 5 seconds. Additionally, an icon 406 representing the payment mode may be displayed.

Referring back to FIG. 2, the WPD device 200 may further include a vibration unit (not shown) in communication with the processor. The vibration unit may be activated in response to receiving the data from the external device to notify the user about receipt of the data. For example, upon receipt of the message by the remote device, the vibration unit of the WPD device 200 may be activated.

In an example embodiment, the band 208 of the WPD device 200 may be detachable. The detached view 220 shows the band 208 detached from the housing 202 of the WPD device 200.

The WPD device 200 may further include a GPS unit (not shown) configured to track geographical location of the device. Such information may be applied for spatial and positional awareness tracking, monitoring position of a child, a senior, or a patient. In some embodiments, the WPD device 200 may connect to one or more external devices (for example, other WPD devices), synchronize with the one or more external devices in real time, tracks a geographical location of the one or more external devices in real time, and provide communication capabilities using an embedded emergency button configured to give a medical alert signal, a request for help signal, or another informational signal. Thus, users may track geographical location of each other.

In some embodiments, access to the WPD device 200 may be protected by a password, a Personal Identification Number code, biometric authorization, and so forth. Biometric authorization may be performed using one or more biometric sensors and may include fingerprint scanning, palm scanning, face scanning, retina scanning, heart rate sensing, and so forth. In some embodiments, fingerprint scanning may be performed using a fingerprint reader integrated in the WPD device 200 or detachably connected to the WPD device. The scanned fingerprint may be matched to one or more approved fingerprints stored in the memory unit of the WPD device 200. The access to the device may be granted if the scanned fingerprint matches one of the stored fingerprints, otherwise access may be denied.

The payment transaction may be associated with a NFC and be performed for purchases online and offline. A payment associated with the payment transaction may be transferred from a pre-paid account of the user or charged to a mobile account of the user or a bank account of the user. The payment may include at least a one-touch and one-scan payment for street parking in demarcated areas. The payment may be performed using a license plate, transponder tags, barcode stickers, and reading the code from the display. A merchant may use a combination of the NFC and the code on the display for performing the one-touch and one-scan payment. The NFC may be used to establish radio communication with the external device by touching the housing of the WPD device 200 and the external device or bringing the housing of the WPD device 200 and the external device into proximity, such a distance of up to 10 centimeters. The processor may be operable to operate in three modes, such as an NFC target mode when the WPD device 200 is acting as a credential, a NFC initiator mode when the WPD device 200 is acting as a reader, and an NFC peer-to-peer mode. The payment may be further associated with advertisement tags, two-dimensional barcodes, and ultra-high frequency tags. The processor may be operable to be connected to a cloud. User credentials may be provisioned over the air. The payment may be associated with a payment application associated with the processor to control transferring of the payment and access payment readers. The NFC unit may be operable to connect to a third-party NFC device with a server for data.

The processor may be associated with an operating system operable to pair with third-party applications running on the external device. The processor may integrate a third-party developer technology and the third-party applications and notifications into a form factor. The processor may be operable to download applications. The WPD device 200 may act as or be associated with smart textiles, an activity tracker, a smartwatch, smartglasses, a GPS watch, mixed reality, computer-mediated reality, clothing technology, Smart closing, healthcare, augmenter reality, and smart and connected devices.

The WPD device 200 may be adapted to enable a Bluetooth low energy payment. The WPD device 200 may be further associated with one or more of a transactional payment based on Unstructured Supplementary Service Data, Short Message Service, direct operator billing, a credit card mobile payment, an online wallet, a QR code payment, contactless NFC, a cloud-based mobile payment, an audio signal-based payment, a Bluetooth Low Energy signal beacon payment, an in-application payment, a Software Development Kit payment, an Application Programming Interface payment, a social networking payment, and a direct carrier and bank co-operation.

Figure 5:
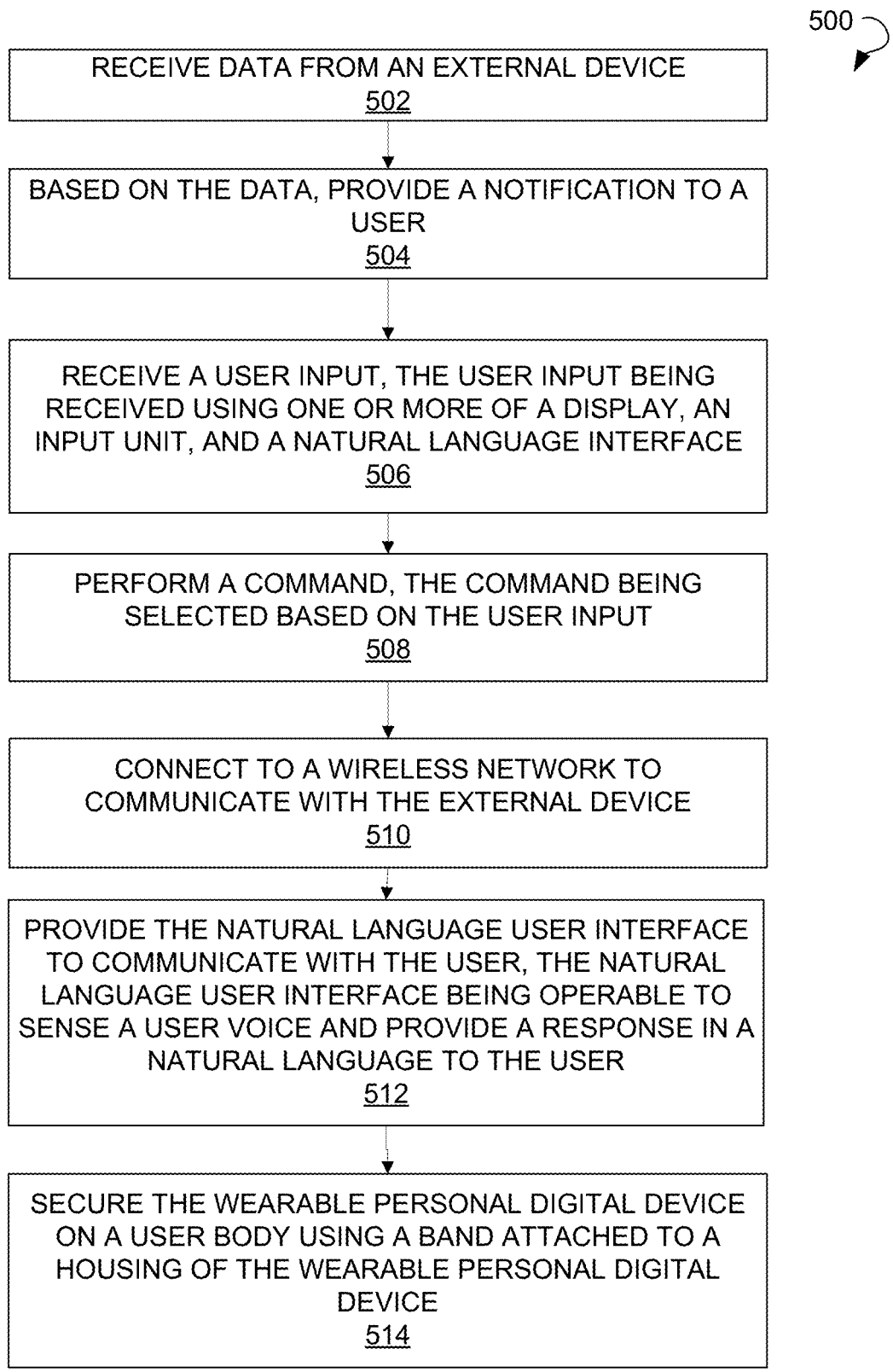
FIG. 5 is a flow chart illustrating a method for facilitating user interaction with a wearable personal digital device for facilitating mobile device payments, personal use, and health care, in accordance with certain embodiments.

FIG. 5 is a flow chart illustrating a method 500 for facilitating user interaction with a WPD device, in accordance with certain embodiments. The method 500 may start with receiving data from an external device at operation 502. Based on the data, a notification may be provided to a user at operation 504. In an example embodiment, providing of the notification includes one or more of the following: providing a vibration, providing a sound, and providing a light indication. At operation 506, a user input may be received. In an example embodiment, the user input may be received using a display, an input unit of the WPD device, or a natural language user interface. At operation 508, a command may be performed. In an example embodiment, the command selected based on the user input may be performed. At operation 510, the WPD device may be connected, using a communication circuit communicatively coupled to the processor of the WPD device, to a wireless network to communicate with the external device.

At operation 512, the natural language user interface may be provided to communicate with the user. The natural language user interface may be operable to sense a user voice and provide a response in a natural language to the user. The WPD device may be secured on a user body at operation 514 using a band attached to a housing of the WPD device.

In an example embodiment, the method 500 may further include capturing, by a camera communicatively coupled to the processor, a code. The code may include a linear dimensional code, a two-dimensional code, a snap tag code, or a QR code. The method 500 may further include reading the code to obtain product information and merchant information encoded in the code. Based on the merchant information, a payment transaction may be initiated.

Additionally, the method 500 may include activating the display based on one or more of the following: a movement of a user hand, a movement of the user body, a gesture performed by the user in proximity to the display, user voice, and the like. In an example embodiment, the method 500 further includes storing the biometric parameters sensed by the one or more biometric sensors to the memory unit of the WPD device. Alternatively, the biometric parameters sensed by the one or more biometric sensors may be transmitted to the external device.

Additionally, the method 500 may include sensing, by a microphone, voice data. The voice data may be obtained from the user and may include a voice command, a voice memo, or a voice message. The voice data may be transmitted to the processor of the WPD device for further processing. Additionally, the voice data may be recognized to obtain a user request. The user request may be transmitted to the external device.

In an example embodiment, the method 500 may further include estimating time of the user input. The user input may include pressing the display by the user. Based on the time, a command may be selected from a table representing relationship between the time of pressing and a plurality of commands. The selected command may be further performed by the processor.

Additionally, the method 500 may include displaying, by the display, data associated with the activity of the user. The activity of the user may include calories burned, sleep quality, breaths per minute, snoring breaks, steps walked, and distance walked. Tumor DNA to be used as a marker for screening, early detection, and monitoring, traces of RNA from cancer cells can be found in a drop of saliva, the RNA is a molecule that plays a key role in the transcription of DNA, the mobile and wearable device screen process by which the genetic material is read in order to detect the proteins by detecting genetic mutations in a protein from epidermal factor receptor, by examining RNA in samples on mobile and wearable screens, and it is therefore possible to tell what sorts of processes are going on inside a cell by seeking out fragments of tumor RNA in saliva, including those associated with cancer. Furthermore, wearable device may be integrated with one or more thin film silicon photonic biosensor that uses beams of light to detect tiny changes in the composition of a saliva or urine sample on the screen of wearable device or mobile device, and which essentially looks at the level of binding between a DNA probe and target microRNA to figure out the level of microRNA in the sample, and this may provide clues to the presence of some types of cancer, cardiac disease, and other serious health issues via artificial intelligence (AI) big data analysis. Biosensors designed to detect a specific biological analyte by essentially converting a biological entity (i.e., protein, DNA, RNA) into an electrical signal that can be detected and analyzed by using of biosensors in cancer detection and monitoring. The biosensors can be designed to detect emerging cancer biomarkers and to determine drug effectiveness at various target sites. The biosensor may have the potential to provide fast and accurate detection, reliable imaging of cancer cells, and monitoring of angiogenesis and cancer metastasis, and the ability to determine the effectiveness of anticancer chemotherapy agents. The method 500 may further include providing data associated with the one or more biometric parameters to be displayed on the display. The one or more biometric parameters may include one or more of the following: a blood pressure, a heart rate, a glucose level, a body temperature, an environment temperature, and arterial properties.

The wearer may monitor CAR-T cell therapy by separating the peripheral blood of the bearer patient immune T cells in vitro sterile culture, and then genetically engineered and modified, it is based on the type of tumor specificity of patients suffering from genetic modification and in vitro expansion, and finally the wearer patient reinfusion body, achieve the purpose of killing tumor cells. The wearer may further monitor CAR-T cell preparation, insert CAR molecular DNA be integrated into human chromosome 19 on the first intron AAVSI site, the donor DNA sequence provided in the CAR molecule containing a sequence upstream of the receptor sequences and AAVSI cut left arm sequence homology, CAR downstream molecule containing poly-A sequence and AAVSI the right arm sequence homology. The wearer furthermore monitor gene edited T cells applications to use the antibody molecules of various types of tumor surface antigens into the application of human T cell genome AAVSI sites. To avoid potential off-target effects, a mutant enzyme of Ni ckase Cas9 may be used to only cut off a strand of DNA, the single-stranded gap will promote homologous recombination, therefore, to insert CAR molecules precisely integrated into human T cell genome specific "safe harbor" sites, which may not affect the function of any normal human gene, avoiding the use of viral vectors security risks and exogenous gene transit may insert a series of fatal risk of genetic toxicity and immunogenicity of the genome, and may integrate various types of tumor surface antigen receptor to human T cell genome AAVSI site express specific receptors for all types of tumor-specific T cells recognize and kill tumor cells. The wearer may monitor a chimeric antigen receptor (CAR) T cells and a preparation method can allograft, aimed at resolving existing T cell separation difficulties from patient own self, who cannot effectively kill tumor cells and mixed with the issue of tumor cells. Another kind T cells can allograft chimeric T cell antigen receptor, said chimeric T cell antigen receptors including T cell receptors and a chimeric antigen. The T cell is a genetically engineered allogeneic transplantation can T cells. The allograft may be chimeric T cell antigen receptor, and the T cells through gene knockout in a specific point of genetically modified T cells. The allograft may be chimeric T cell antigen receptor, and said specific gene of TCR gene, including the TCR [alpha] chain and a β chain, said genetically modified specifically: α in the TCR and corresponding foreign gene encoding β-chain of one or two chain constant region exon by gene knockout point, the TCR of T cells is not active, and thus T cells can be allogeneic. The allograft may be chimeric T cell antigen receptor, and said chimeric antigen receptor by a scFv antigen binding sequence, a transmembrane sequence, and intracellular signal transduction sequence. The allograft may be chimeric T cell antigen receptor, and said scFv antigen binding sequence comprises a light chain variable region sequence and a heavy chain variable region sequence. The allograft may be chimeric T cell antigen receptor, and the transmembrane sequence is CD8. The intracellular signal transduction sequence may comprise the CD28 extracellular domain sequence, the sequence and the intracellular domain of 4-1BB intracellular CD3G domain sequences. A species, may allograft chimeric antigen receptor T cells, which comprises of the TCR α and β chains of one or both chains constant outside the corresponding region of the gene coding exon, the T cells TCR is not active, and then be able to obtain allogeneic T cells, and furthermore carrying the chimeric receptor antigen lentivirus infection can be obtained by the above-described allogeneic T cells can be obtained after completion of infection allogeneic chimeric T cell antigen receptor. The wearer may monitor T cells genetically engineered, in turn, can make this T cell allografts without causing immune rejection. Then this will not produce allograft immune rejection T cell binding third-generation CAR can prepare an allograft universal chimeric antigen receptor T cells to tumor therapy.

In an example embodiment, the method 500 may further include sensing a rotational motion of the input unit. The input unit may be rotated by the user. Based on the sensing, the data displayed on the display may be scrolled. Additionally, the method 500 may include activating a vibration unit in response to receiving the data from the external device to notify the user about receipt of the data.

Figure 6:
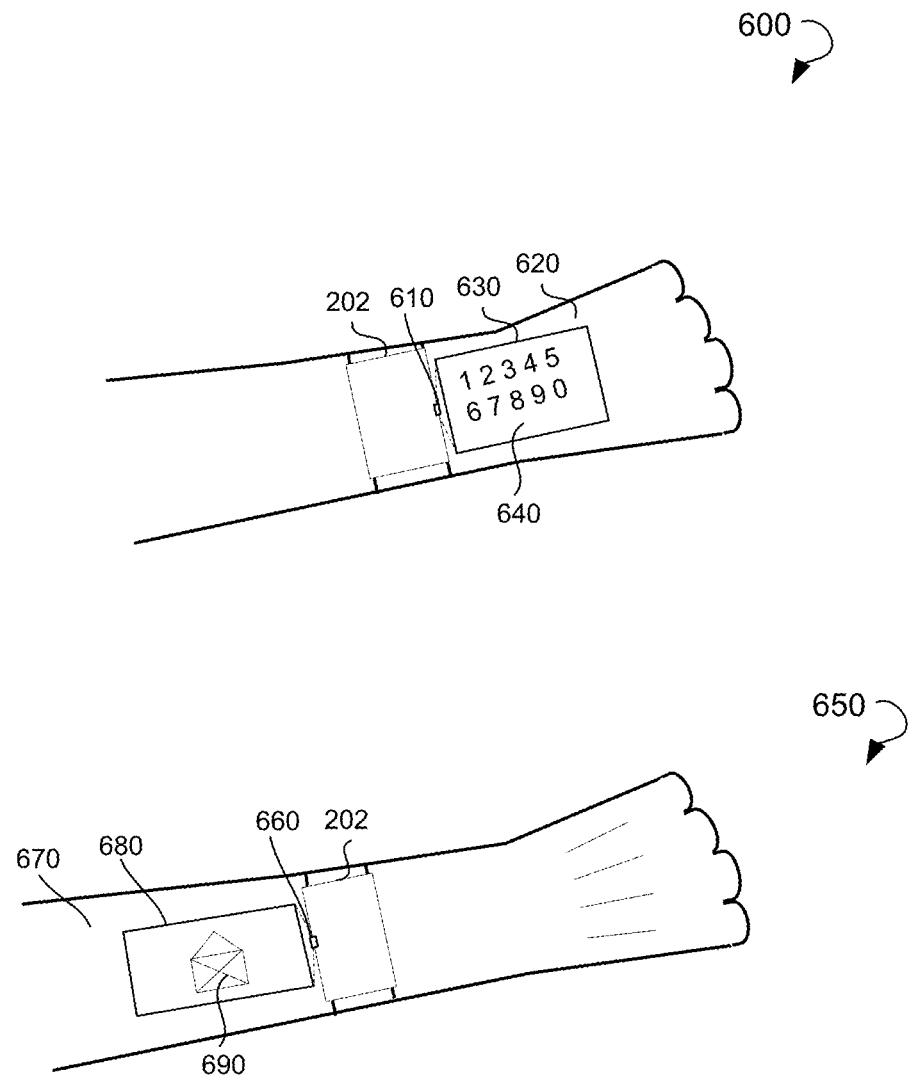
FIG. 6 illustrates an example of wearable personal digital devices for facilitating mobile device payments, personal use, and health care, in accordance with some embodiments.

FIG. 6 shows schematic representations of WPD devices 600 and 650, according to example embodiments. The WPD device 600 may include a housing 202 that may enclose the elements of the WPD device 600 as described above with reference to FIG. 2. The WPD device 600 may include a projector 610. The projector 610 may project a data onto a viewing surface 620 to form a display area 630. The display area 630 may serve as a further display of the WPD device 600. The viewing surface 620 may include a hand of the user. The data shown on the display area 630 may include any data requested by the user or any incoming notifications or alerts, including a virtual keyboard, a notification of the external device, time, data requested by the user, a caller name, a text message, a reminder, a social media alert, an email, a weather alert, and the like. FIG. 6 shows a virtual keyboard 640 displayed on the hand of the user.

The WPD device 650 may include a housing 202 that may enclose the elements of the WPD device 600 as described above with reference to FIG. 2. The WPD device 650 may include a projector 660. The projector 660 may project a data onto a viewing surface 670 to form a display area 680. The display area 680 may serve as a further display of the WPD device 650. The data shown on the display area 680 may include a message 690.

As shown on FIG. 6, the projector may be disposed on any side of the housing 202. More specifically, the display area 630 may be provided to the right from the wrist of the user (as in the WPD device 600) or the display area 680 may be provided to the left from the wrist of the user (as in the WPD device 650).

Figure 7:
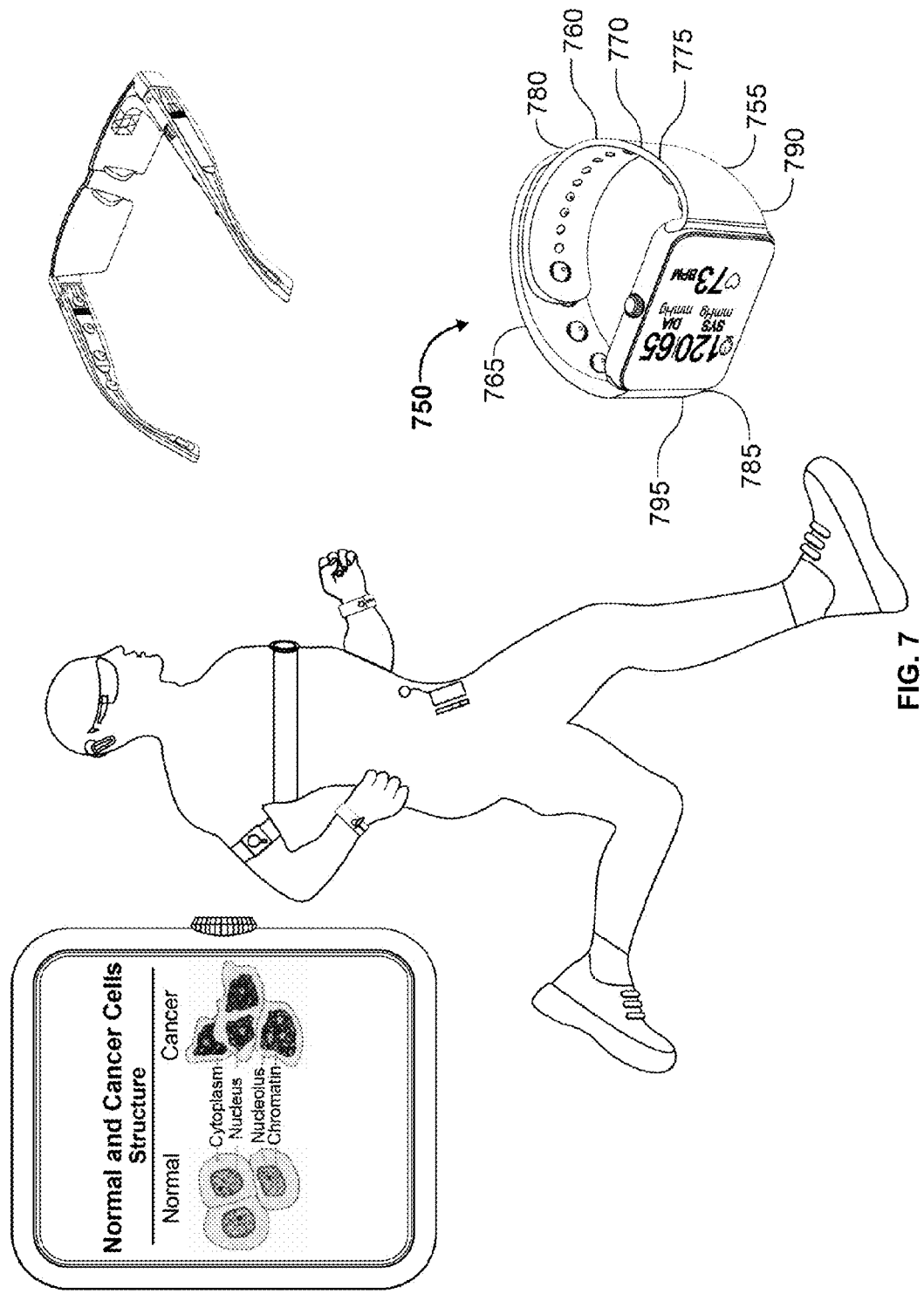
FIG. 7 illustrates an example of wearable personal digital devices for facilitating mobile device payments, personal use, and health care, in accordance with some embodiments.

FIG. 7 shows a man running and wearing various wearables with a sensor, e.g. smart glasses, smartwatch, etc. The sensor consists of a tri-axial accelerometer, a microcontroller and a Bluetooth Low Energy transceiver. Cancer may be detected using Temperature Variation and Radiation Analysis (TVRA) via wearable device, which has grown tangibly due to many factors, such as at least life expectancies increase, personal habits and ultraviolet radiation exposures. The smartwatch can display various medical parameters received from the wearables and also display differences between normal and cancerous cell structure.

FIG. 7 further shows the WPD device 750, which may be configured to be rolled around a wrist of the user. The WPD device 750 may include a processor 755, a projector 760, activity tracking sensors 765, a communication circuit including a Bluetooth module 770 or a Wi-Fi module 775, a haptic touch control actuator 780, a memory unit 785, an indicator 790, such as a LED, and a charging unit 795.

Figure 8:
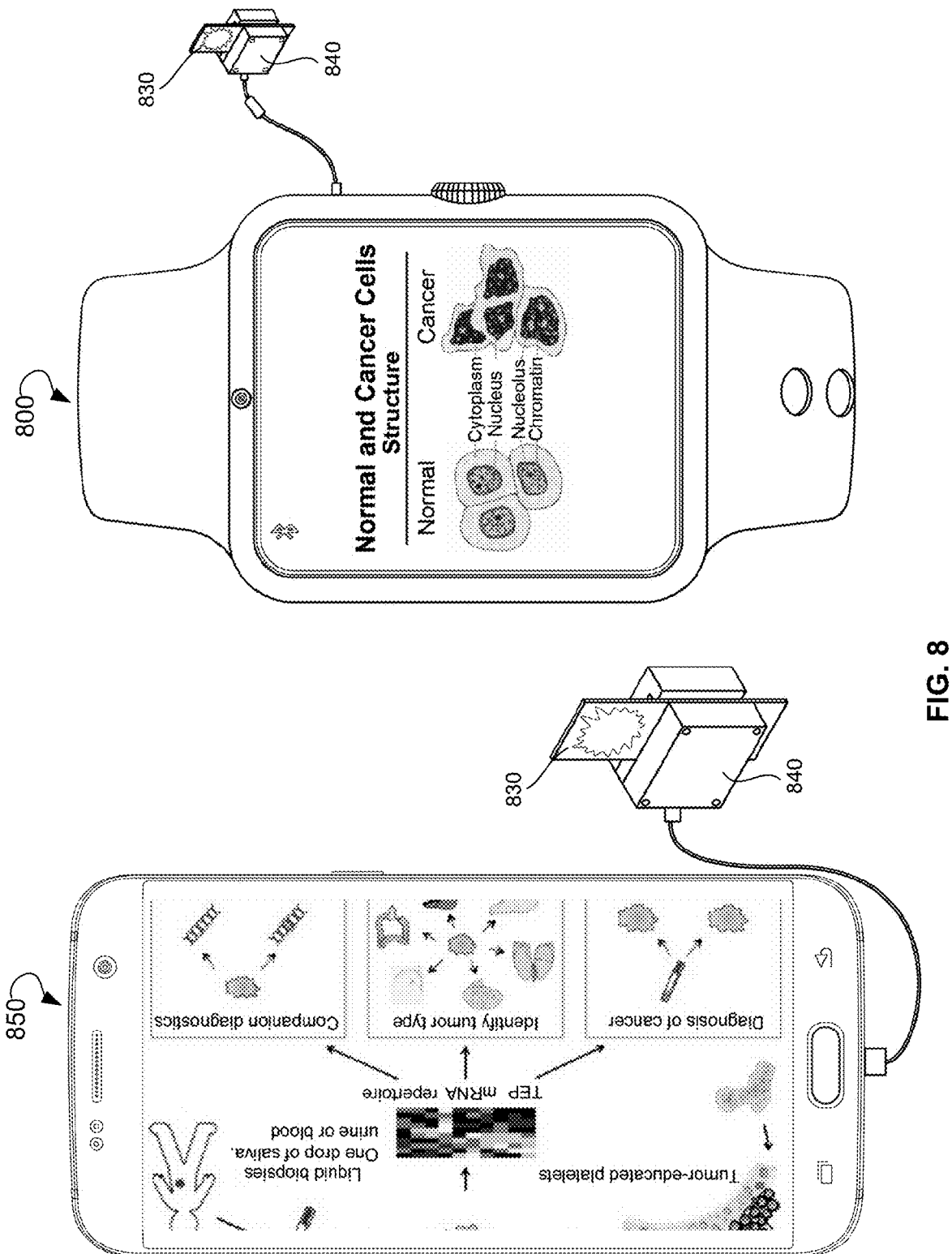
FIG. 8 illustrates an example of wearable personal digital devices for facilitating mobile device payments, personal use, and health care, in accordance with some embodiments.

FIG. 8 shows a mobile device 850 and smartwatch 800, which are wire connected to a thin film silicon photonic biosensor 840. The biosensor 840 may use beams of light to detect tiny changes in the composition of a saliva or urine sample on a thin film 830. The film 830 when pressed against the skin may create changes in electrical current and light (ECL) that can be captured by a high-quality digital camera of a wearable device. Normal and cancerous cell structures are displayed on a screen of the mobile device 850 and smartwatch 800.

Figure 9:
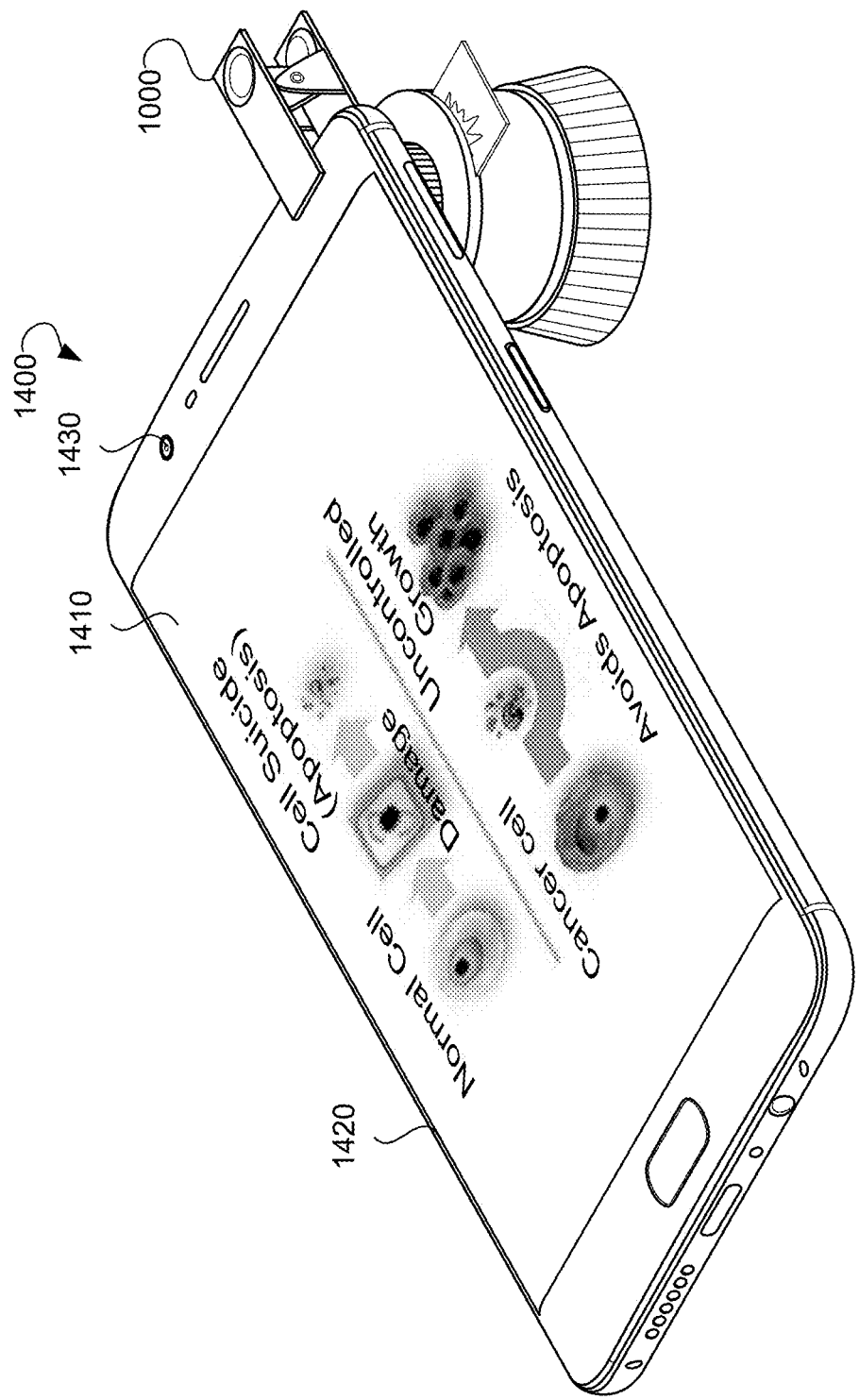
FIG. 9 illustrates an artificial intelligence wearable and mobile personal digital device for facilitating mobile device payments, personal saliva testing, personal use, and health care being a of healthcare saliva testing device for point of healthcare saliva testing, according to an example embodiment.

FIG. 9 shows an AI wearable and mobile personal digital device 1400 for facilitating mobile device payments, personal saliva testing, personal use, and health care being a POH saliva testing device for POH saliva testing. The AI wearable and mobile personal digital device 1400 may include a processor (not shown). The processor may be operable to receive data from an external device associated with POH saliva testing. Based on the data, the processor may provide a notification to a user. The processor may be further configured to receive a user input and perform a command, which may be selected based on the user input. The processor may be further operable to provide a natural language user interface to communicate with the user. The natural language user interface may be operable to sense a user voice and provide a response in a natural language to the user. The AI wearable and mobile personal digital device 1400 may include a near field communication (NFC) unit communicatively coupled to the processor and a display 1410 communicatively coupled to the processor. The display 1410 may include a touchscreen. The display 1410 may further include a force sensor operable to sense a touch force applied by the user to the display 1410 and calculate coordinates of a touch by the user, and further operable to analyze the touch force and, based on the touch force, select a tap command or a press command based on a predetermined criteria.

The AI wearable and mobile personal digital device 1400 may include a projector (such as the projector 660 as shown on FIG. 6) communicatively coupled to the processor. The projector may be operable to project a data onto a viewing surface external to the AI wearable and mobile personal digital device 1400. The data may include a virtual keyboard operable to input commands to the processor and one or more of the following: the notification of the external device, time, and data requested by the user, a caller name, a text message, a reminder, a social media alert, an email, a weather alert, and so forth.

The AI wearable and mobile personal digital device 1400 may include a timepiece unit communicatively coupled to the processor and configured to provide time data. The AI wearable and mobile personal digital device 1400 may further include one or more activity tracking sensors communicatively coupled to the processor to track activity of the user. The one or more activity tracking sensors may be operable to track snoring and, based on tracking of the snoring, produce an alarm to break snoring. The AI wearable and mobile personal digital device 1400 may further include a memory unit communicatively coupled to the processor, and a communication circuit communicatively coupled to the processor and operable to connect to a wireless network and communicate with the external device. The AI wearable and mobile personal digital device 1400 may include a housing 1420 adapted to enclose at least the processor, the display 1410, the one or more activity tracking sensors, the memory unit, and the communication circuit.

The AI wearable and mobile personal digital device 1400 may further include an input unit communicatively coupled to the processor. The input unit may extend from the housing and may be configured to perform one or more of a rotational motion and a linear motion. The one or more motions may be operable to input commands to the processor.

The AI wearable and mobile personal digital device 1400 may further include a band adapted to attach to the housing 1420 and to secure the AI wearable and mobile personal digital device 1400 on a user body. More specifically, the AI wearable and mobile personal digital device may include a wristwatch.

The AI wearable and mobile personal digital device 1400 may further include one or more biometric sensors disposed within the band and operable to sense one or more biometric parameters of the user. Based on detection that the one or more of the biometric parameters exceed predetermined limits, the one or more biometric sensors may be configured to produce the alarm. The one or more biometric sensors may include lenses operable to use infrared LEDs and visible-light LEDs to sense a heart rate of the user. The one or more biometric sensors may include a skin contact sensor data engine. The skin contact sensor data engine may be operable to monitor an electrocardiogram of the user and the heart rate of the user. The electrocardiogram and the heart rate may be identification and personal data of the user. The skin contact sensor data engine may be operable to prompt the user to enter a personal identification number and associate the personal identification number with both the electrocardiogram and the heart rate obtained after the AI wearable and mobile personal device 1400 has been secured to a wrist of the user. The electrocardiogram and the heart rate may be stored in the memory unit as a reference electrocardiogram and a reference heart rate.

Additionally, a thermal infrared (IR) measurement of the one or more biometric sensors may be used to investigate a potential of cancer detection. The one or more biometric sensors may include an adhesive sensor system worn on the skin that automatically detects human falls and fatal diseases, a sensor consisting of a tri-axial accelerometer, a microcontroller, and a Bluetooth Low Energy transceiver and worn on the user body to detect a biological analyte by converting a biological entity into an electrical signal to be detected and analyzed by using a biosensor in cancer and fatal diseases detection and monitoring.

The AI wearable and mobile personal digital device 1400 may further include a haptic touch control actuator operable to produce a haptic feedback in response to one or more events. The one or more events may include receiving of the alert, receiving of a notification, a confirmation, movement of the AI wearable and mobile personal digital device, receiving of the user input, and sensing of the one or more biometric parameters. The haptic feedback may be sensed by the user body. The haptic feedback may include a plurality of feedback types. Each of the one or more events may be associated with one of the plurality of feedback types. The user input may be received using one or more of the display, the input unit, and the natural language user interface.

The AI wearable and mobile personal digital device 1400 may further include a battery disposed in the housing 1420 and a magnetic inductive charging unit operable to magnetically connect to the housing 1420 and wirelessly connect to the battery. The magnetic inductive charging unit may be operable to wirelessly transfer energy to the battery. The magnetic inductive charging unit may be integrated into the housing 1420.

The AI wearable and mobile personal digital device 1400 may further include a camera 1430 communicatively coupled to the processor and operable to capture a code. The code may include one or more of the following: a linear dimensional barcode, a two-dimensional barcode, a snap tag code, and a Quick Response (QR) code. The processor may be further operable to read the code to obtain one or more of a product information and a merchant information encoded in the code and, based on the merchant information, initiate a payment transaction. The payment transaction may be performed by sending payment data by the NFC unit to a merchant using the NFC.

The AI wearable and mobile personal digital device 1400 may further include a swipe card reader communicatively coupled to the processor and operable to read data of a payment card swiped through the swipe card reader. The data may be transmitted to the processor or the external device.

The processor may be further operable to generate, based on user payment data and user personal data, a unique code encoding the user payment data and the user personal data. The user payment data and the user personal data may be stored in the memory unit. The processor may be further operable to prompt the user to touch the display to scan user fingerprints, determine the heart rate and the electrocardiogram of the user to obtain determined heart rate and determined electrocardiogram, and compare the scanned user fingerprints, the heart rate and the user electrocardiogram with reference fingerprints stored in the memory unit, the reference heart rate, and the reference electrocardiogram. The processor may be further operable to detect matches of the scanned user fingerprints with the reference fingerprints, the determined heart rate with the reference heart rate, and the determined electrocardiogram with the reference electrocardiogram. After the detecting of the matches, the processor may provide the unique code via the display to a merchant digital device associated with one or more of a healthcare center, a hospital, an emergency center, and a saliva research center for performing the payment transaction. Upon performing the payment transaction, the processor may provide a payment confirmation to the user.

Figure 10:
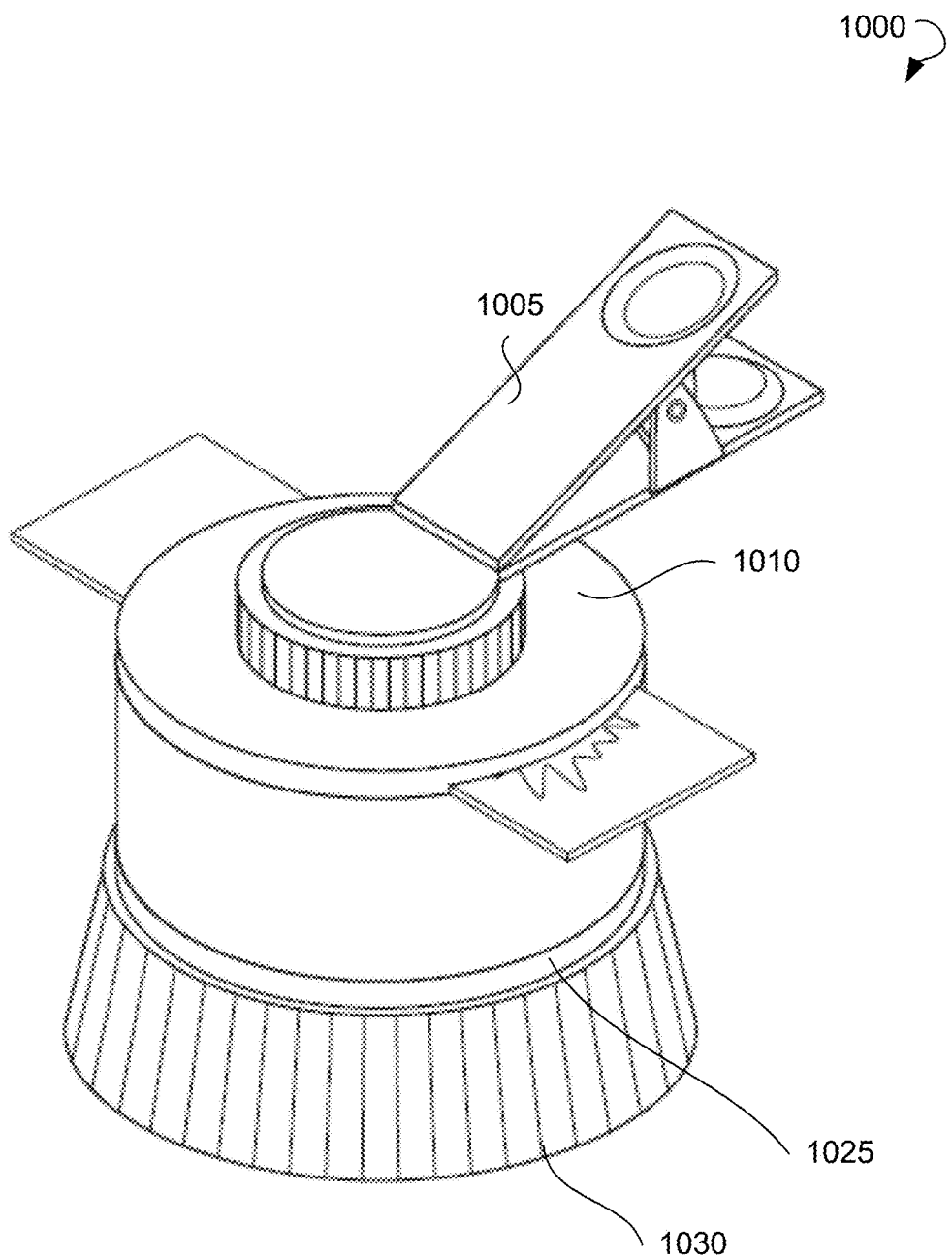
FIG. 10 shows a point of healthcare saliva testing device for point of healthcare saliva testing being a component of an artificial intelligence wearable and mobile personal digital device for facilitating mobile device payments, personal saliva testing, personal use, and health care, according to an example embodiment.
Figure 11:
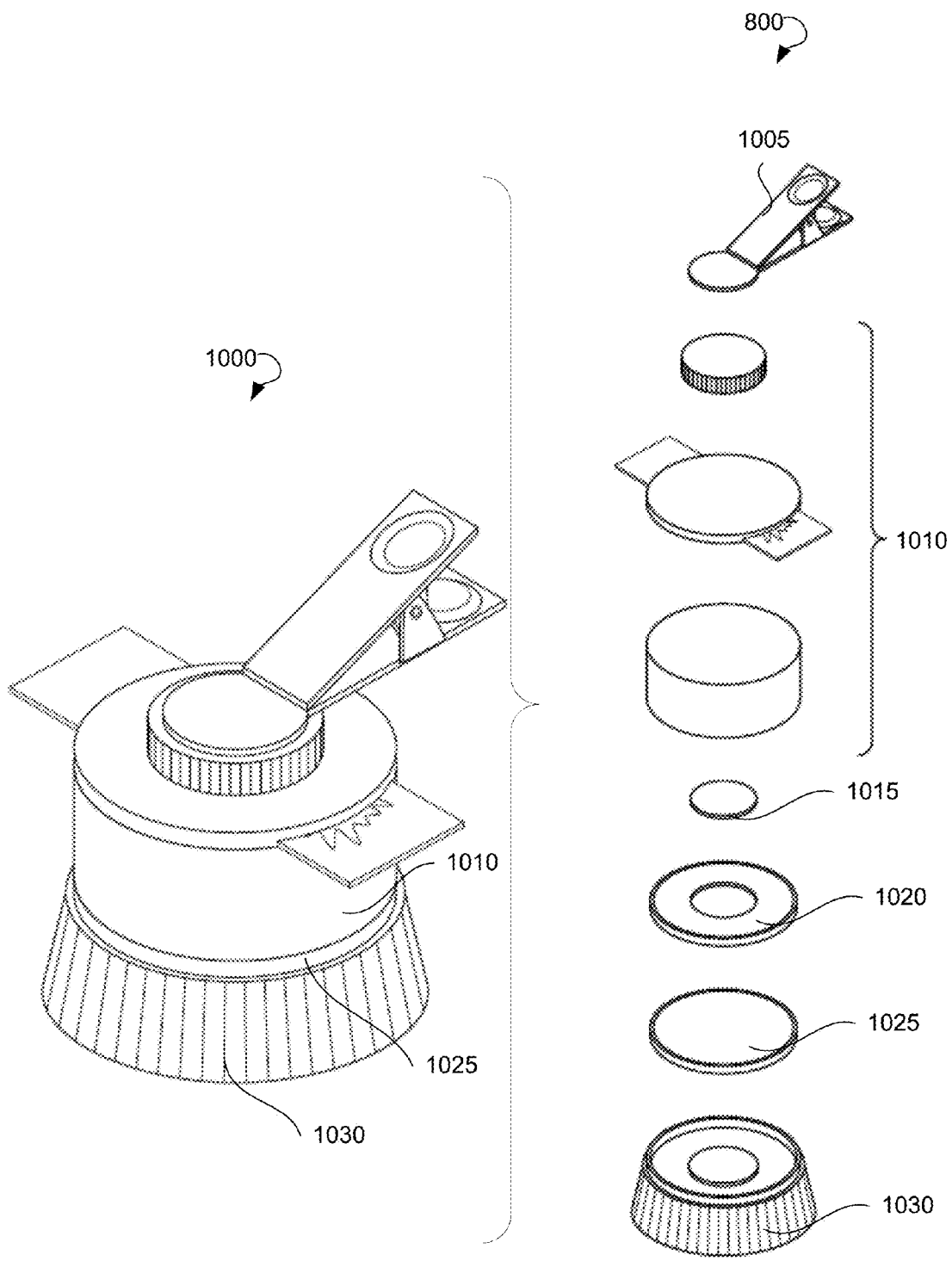
FIG. 11 shows a point of healthcare saliva testing device for point of healthcare saliva testing being a component of an artificial intelligence wearable and mobile personal digital device for facilitating mobile device payments, personal saliva testing, personal use, and health care, according to an example embodiment.

FIGS. 10 and 11 show a point of healthcare (POH) saliva testing device 1000 for POH saliva testing being a component of an artificial intelligence (AI) wearable and mobile personal digital device for facilitating mobile device payments, personal saliva testing, personal use, and health care, according to an example embodiment. The POH saliva testing device 1000 may be used together with the AI wearable and mobile personal digital device for facilitating mobile device payments, personal saliva testing, personal use, and health care, as shown on FIG. 9. The POH saliva testing device 1000 may include a mounting clip 1005, a saliva sample insert apparatus 1010, a pinhole 1015, a light-emitting diode (LED) board 1020, a battery 1025, and a set of sensors 1030.

Figure 12:
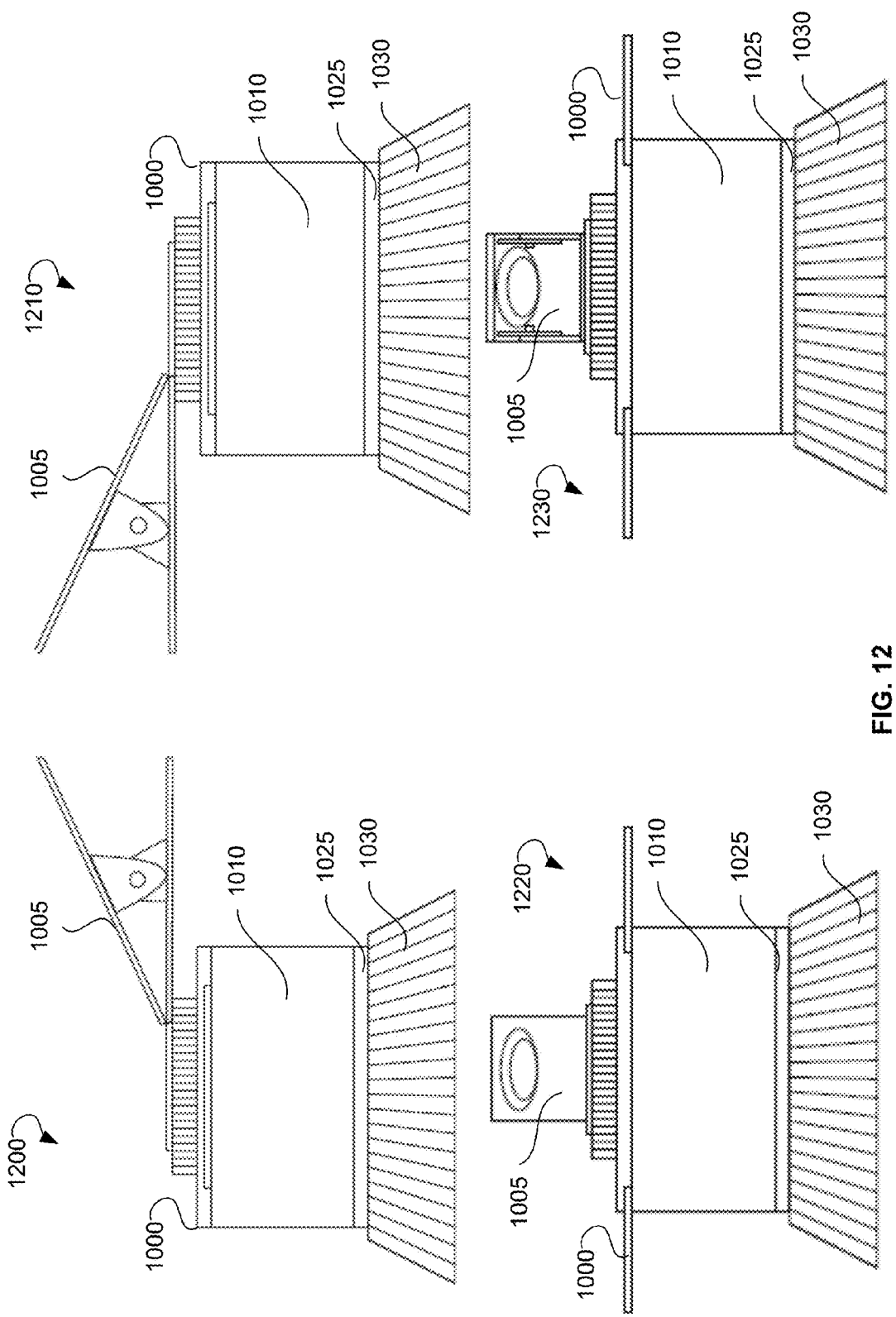
FIG. 12 shows a right side view of the point of healthcare saliva testing device, a left side view of the point of healthcare saliva testing device, a front view of the point of healthcare saliva testing device, and a rear view of the point of healthcare saliva testing device, according to an example embodiment.

FIG. 12 shows a right side view 1200 of the POH saliva testing device 1000, a left side view 1210 of the POH saliva testing device 1000, a front view 1220 of the POH saliva testing device 1000, and a rear view 1230 of the POH saliva testing device 1000, according to an example embodiment.

Figure 13:
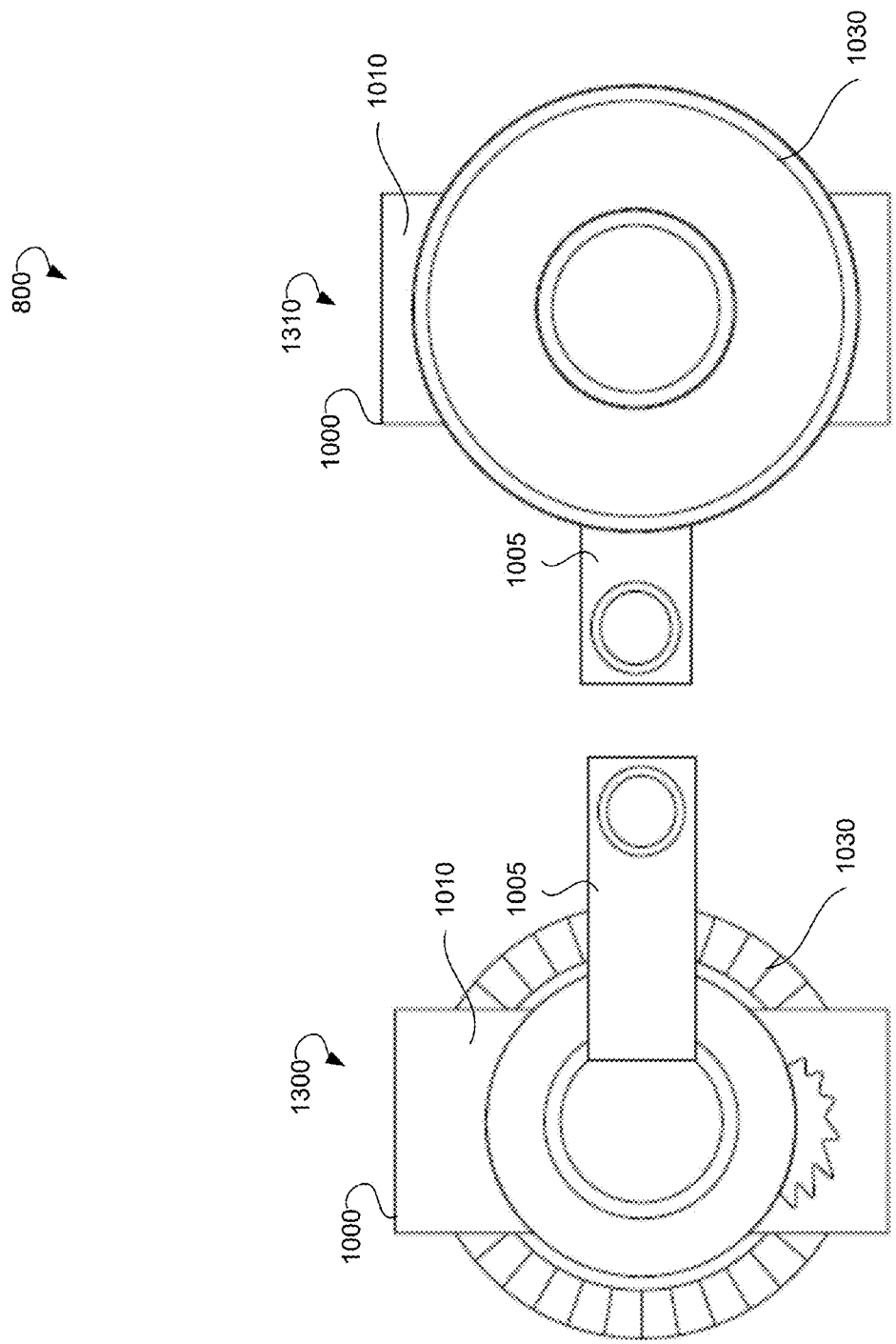
FIG. 13 shows a top view of the point of healthcare saliva testing device and a bottom view of the point of healthcare saliva testing device, according to an example embodiment.

FIG. 13 shows a top view 1300 of the POH saliva testing device 1000 and a bottom view 1310 of the POH saliva testing device 1000, according to an example embodiment.

Figure 14:
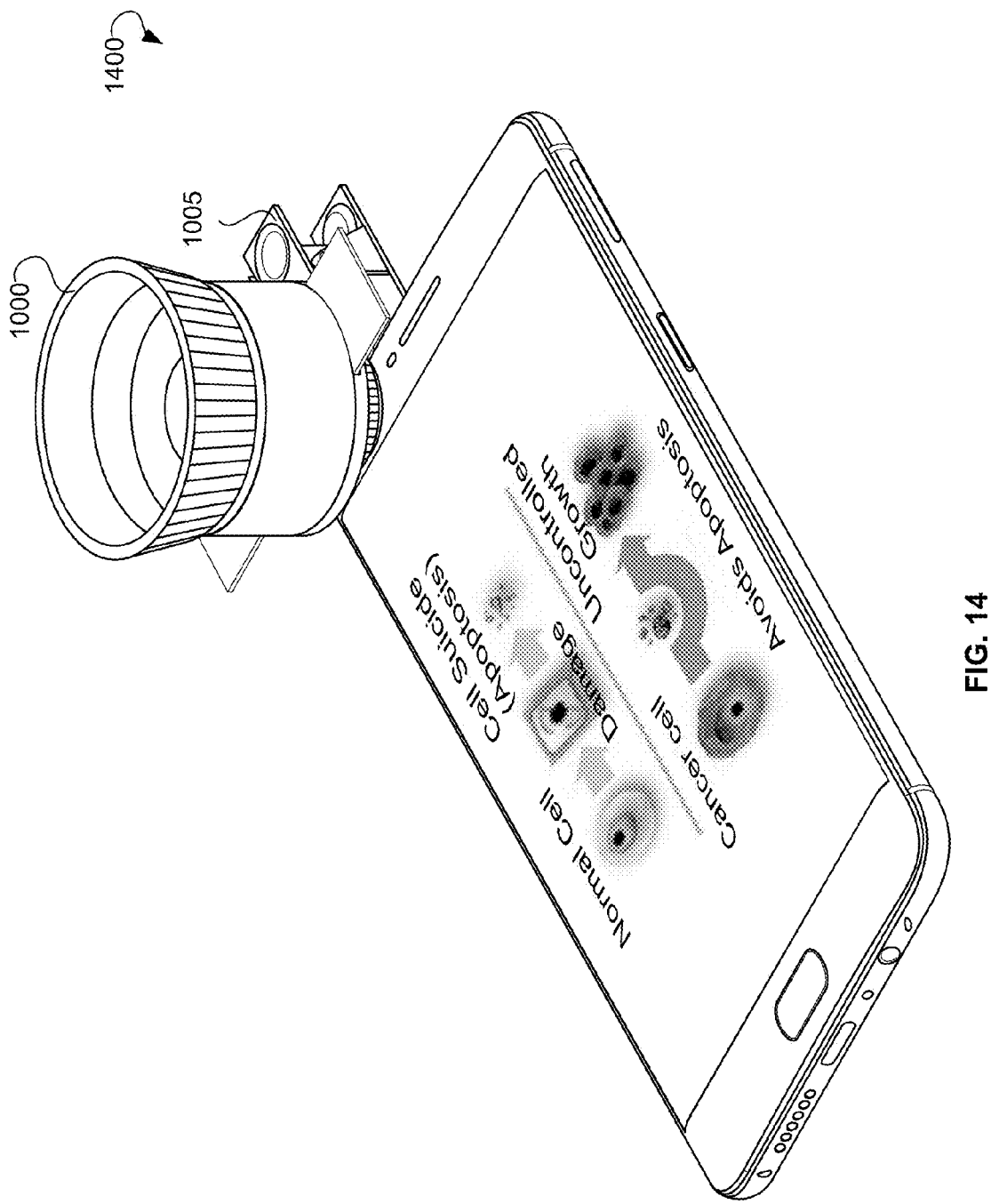
FIG. 14 shows a general view of an artificial intelligence wearable and mobile personal digital device with a POH saliva testing device for point of healthcare saliva testing, according to an example embodiment.

FIG. 14 shows a general view of an AI wearable and mobile personal digital device 1400 with a POH saliva testing device 1000 for POH saliva testing. The POH saliva testing device 1000 may be attached using the mounting clip 1005 to the AI wearable and mobile personal digital device 1400. In an example embodiment, the POH saliva testing device 1000 may be attached to a portion of the AI wearable and mobile personal digital device 1400 where the camera of the AI wearable and mobile personal digital device 1400 is disposed.

The processor AI wearable and mobile personal digital device 1400 may be further configured to transmit the user request to one or more of the external device, the health care center, the hospital, the emergency center, the saliva research center, deoxyribonucleic acid (DNA) genetic testing and analysis authorities, and the like authorities.

In an example embodiment, the POH saliva testing includes a diagnostic technique that involves an analysis of a saliva of the user to identify markers of one or more of endocrine, immunologic, inflammatory, infectious, and health conditions. The POH saliva testing may use a biological fluid for assaying steroid hormones including cortisol, genetic material including ribonucleic acid (RNA), proteins including enzymes and antibodies, and a plurality of substances including natural metabolites, a saliva nitrite, a biomarker for a nitric oxide status, a Cardiovascular Disease, a Nitric Oxide, a salivary biomarker for cardioprotection. The POH saliva testing may be used to screen for and diagnose a plurality of health conditions and disease states including Cushing's disease, anovulation, HIV, cancer, parasites, hypogonadism, and allergies. The POH saliva testing may be further used to assess circadian rhythm shifts in astronauts before flight and to evaluate hormonal profiles of soldiers undergoing military survival training. The POH saliva testing may be performed as a POH saliva testing cite to provide collection, safety, non-invasiveness, affordability, accuracy, and capacity to circumvent venipuncture as compared to blood testing and a plurality of types of diagnostic testing. Upon obtaining multiple saliva samples, the POH saliva testing may be used to perform chronobiological assessments spanning hours, days, or weeks. Collecting a whole saliva by passive drool during the POH saliva testing facilitates increasing a size of sample collection to allow the saliva samples to be tested for a plurality of biomarkers, freezing a left over specimen of a saliva sample of the saliva samples to be further used, to eliminate contamination by eliminating extra saliva collection devices and a need to induce a saliva flow. The POH saliva testing may provide for detection of steroid hormones and antibodies in the saliva sample, additional proteins, genetic material, and markers of nutritional status.

In a further example embodiment, the POH saliva testing may include testing saliva components using a glucose test or a cholesterol test. The glucose test and the cholesterol test may be grouped together into a POH saliva panel. The POH saliva testing may be used in health care to determine physiological and biochemical states including a disease, a mineral content, pharmaceutical drug effectiveness, and organ function of the user, and to detect drug abuse in drug tests. The POH saliva panel may include a basic metabolic panel or a complete saliva count. The basic saliva panel may measure sodium, potassium, chloride, bicarbonate, blood urea nitrogen (BUN), magnesium, creatinine, glucose, and calcium. The POH saliva testing may include tests on cholesterol levels to determine a total cholesterol level, a low-density lipoprotein (LDL) cholesterol level, a high-density lipoprotein (HDL) cholesterol level, and a triglyceride level.

In a further example embodiment, the POH saliva testing may be associated with salivary glands of a human including parotid glands, submandibular glands, sublingual glands, and minor salivary glands. The salivary glands and the minor salivary glands secrete a mixture of salivary components including biological chemicals, electrolytes, proteins, genetic material, and polysaccharides. The mixture of salivary components enters an acinus and duct system of the salivary gland from surrounding capillaries via an intervening tissue fluid. A plurality of substances are produced within the salivary glands. A level of each of the salivary components varies depending on a health status of the user and a presence of a disease. Measuring the salivary components in the saliva is used to screen for infections, allergies, hormonal disturbances, and neoplasms.

The POH saliva testing may include detecting conditions including one or more of the following: a Cushing's disease; an Addison's disease, altered female hormone states including polycystic ovary syndrome, menopause, anovulation, and hormonal alterations in cycling women; altered male hormone states including hypogonadism, andropause, and hyperestrogenicstates; metabolic disturbances including insulin resistance, diabetes, and metabolic syndrome; benign and metastatic neoplasms including breast cancer, pancreatic cancer, and oral cancer; infectious conditions including HIV, viral hepatitis, amoebiasis, and *helicobacter pylori* infection; allergic conditions including food allergy, and other diseases and disorders.

The POH saliva testing may include a personal genome testing to provide a health and carrier status for users having a genetic disease. The POH saliva testing is used to test for a genetic carrier disease including Bloom Syndrome; a recessive gene disorder associated with height disorders and a predisposition to develop cancer. The POH saliva testing may be used to test the user for one or more diseases selected from the following: a Parkinson's disease, a nervous system disorder impacting movement, a Late-onset Alzheimer's disease, a progressive brain disorder destroying memory and thinking skills, a Celiac disease, a disorder resulting in inability to digest gluten, an Alpha-1 antitrypsin deficiency, a disorder that raises a risk of lung and liver disease, early-onset primary dystonia, a movement disorder involving involuntary muscle contractions and uncontrolled movements, factor XI deficiency, a blood-clotting disorder, Gaucher disease type 1, an organ and tissue disorder, Glucose-6-Phosphate Dehydrogenase (G6PD) deficiency, a red blood cell condition, hereditary hemochromatosis, an iron overload disorder, hereditary thrombophilia, a blood-clot disorder, and other diseases.

In a further example embodiment, the POH saliva testing is used in clinical and experimental psychological settings to investigate psychological phenomenon including anxiety, depression, a posttraumatic stress disorder, and behavioral disorders. The POH saliva testing may be used to test a cortisol level and an alpha amylase level being indicative of a stress level. The cortisol level may correlate with the stress level, and the cortisol level rises slowly over time and takes time to return to a base level, thereby indicating that cortisol is associated with a chronic stress level. The alpha amylase level spikes when confronted with a stressor and returns to base level after the stress, thereby making measurement of the alpha amylase level to be a psychological research studying acute stress responses. Saliva samples to test the cortisol level and the alpha amylase level are collected from users by having the users drool through a straw into a collection tube while experiencing a stimulus. The saliva samples are taken at a predetermined interval to record a gradual change in the cortisol level and the alpha amylase level. The collecting of saliva samples is non-invasive. The cortisol level corresponds to experiencing physiological symptoms of nervousness by the users including a heart rate, sweating, and skin conductance. The testing of the alpha amylase level in the saliva samples provides examining sympathoadrenal medullary (SAM) activity. The alpha amylase level correlates with autonomic nervous system activity levels and reacts to a hormone being norepinephrine.

The POH saliva testing may include human immunodeficiency virus (HIV) testing to find a lentivirus being a subgroup of retrovirus and causing a HIV infection and acquired immunodeficiency syndrome (AIDS). AIDS is a condition in humans in which progressive failure of the immune system leads to occurring of life-threatening opportunistic infections and cancers. In absence of treatment, average survival time after being infected with HIV is about 9 to 11 years, depending on the HIV subtype. Infecting with HIV may be performed by the transfer of blood, pre-ejaculate, semen, vaginal fluid, or breast milk. Within these bodily fluids, HIV is present as both free virus particles and virus within infected immune cells. The HIV infects vital cells in a human immune system including helper T cells including $CD4^+$ T cells, macrophages, and dendritic cells. The HIV infection results in lowering levels of the $CD4^+$ T cells through a plurality of mechanisms including pyroptosis of abortively infected T cells, apoptosis of uninfected bystander cells, direct viral killing of infected cells, and killing of infected $CD4^+$ T cells by CD8 cytotoxic lymphocytes that recognize infected $CD4^+$ T cells. When a decline of $CD4^+$ T cell numbers becomes below a critical level, cell-mediated immunity may be lost, resulting in the body becoming progressively more susceptible to opportunistic infections.

Figure 15:
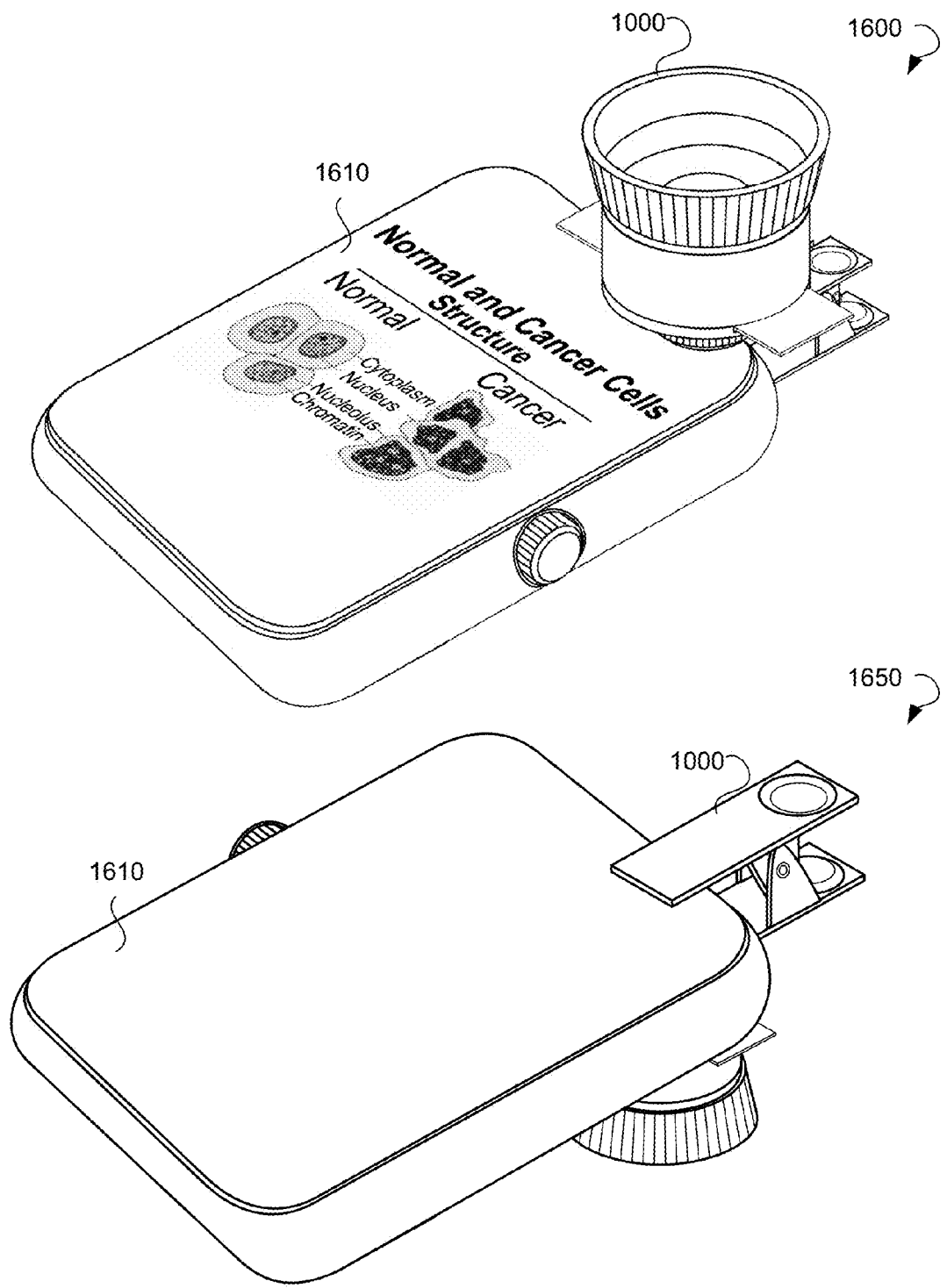
FIG. 15 shows schematic representations representing a wearable and mobile personal digital device for facilitating mobile device payments, personal saliva testing, personal use, and health care, and being a POH saliva testing device for point of healthcare saliva testing, in which the wearable and mobile personal digital device is a smartwatch, according to an example embodiment.

FIG. 15 shows schematic representations 1600 and 1650 representing a wearable and mobile personal digital device 1610 for facilitating mobile device payments, personal saliva testing, personal use, and health care, and being a POH saliva testing device 1000 for POH saliva testing, in which the wearable and mobile personal digital device 1610 is a smartwatch.

Figure 16:
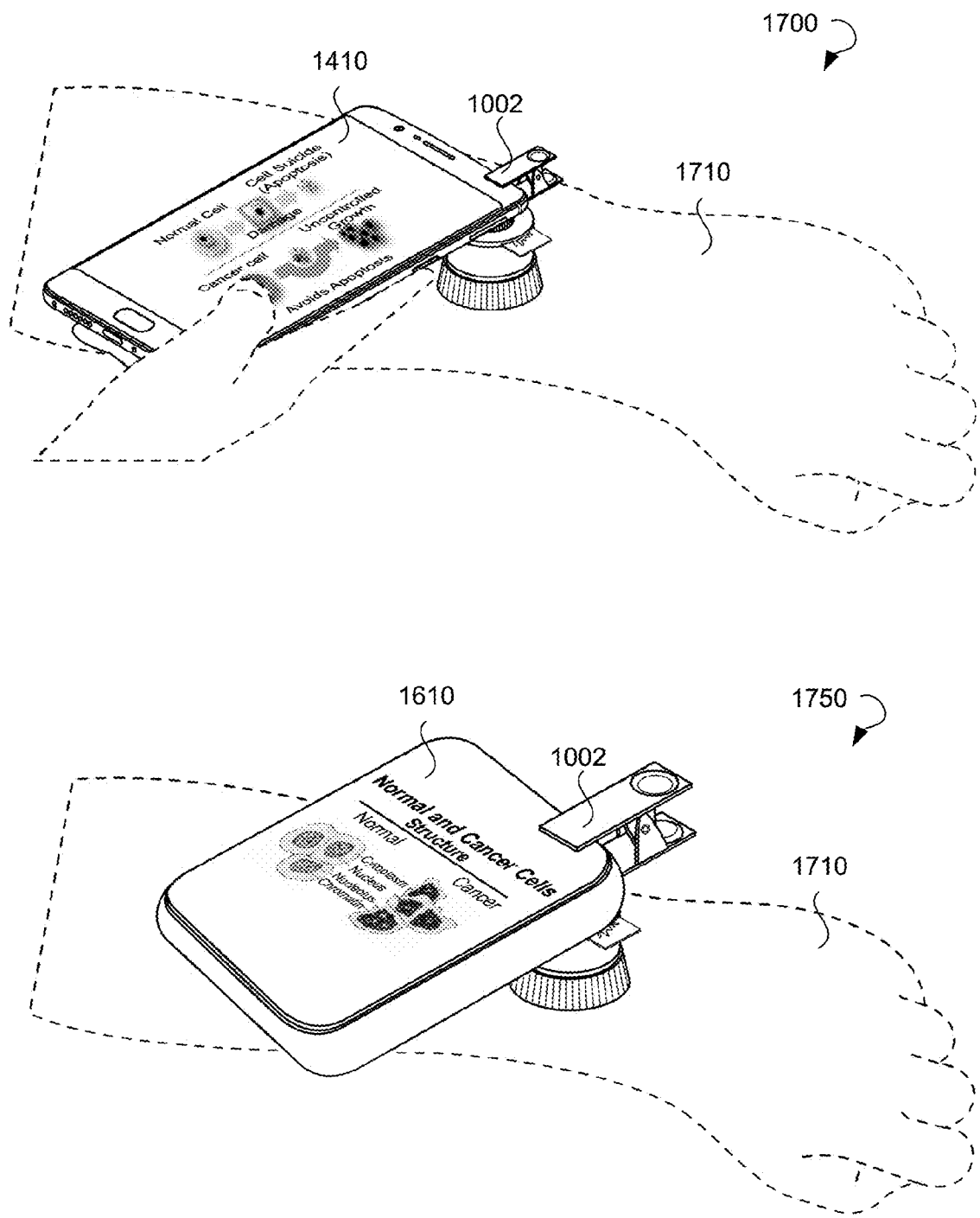
FIG. 16 shows a schematic representation representing a wearable and mobile personal digital device for facilitating mobile device payments, personal saliva testing, personal use, and health care, and being a point of healthcare saliva testing device for point of healthcare saliva testing, in which the wearable and mobile personal digital device is a smartphone and a smartwatch, according to an example embodiment.

FIG. 16 shows a schematic representation 1700 representing a wearable and mobile personal digital device 1410 for facilitating mobile device payments, personal saliva testing, personal use, and health care, and being a POH saliva testing device 1002 for POH saliva testing, in which the wearable and mobile personal digital device 1410 is a smartphone. In the example embodiment shown on FIG. 16, the POH saliva testing device 1002 is the POH saliva testing device as shown on FIG. 11 without a sample insert. More specifically, the POH saliva testing device 1002 may be performed without a saliva sample insert apparatus. The POH saliva testing device 1002 may be used as a POH see-through screening apparatus.

FIG. 16 further shows a schematic representation 1750 representing a wearable and mobile personal digital device 1610 for facilitating mobile device payments, personal saliva testing, personal use, and health care, and being a POH saliva testing device 1002 for POH saliva testing, in which the wearable and mobile personal digital device 1610 is a smartwatch. The schematic representations 1700 and 1750 show that the POH saliva testing device 1002 may be disposed on a hand 1710 of a user to perform testing, such as screening and taking pictures of the skin of the user.

In a further example embodiment, a wearable and mobile personal digital device for facilitating mobile device payments, personal saliva testing, personal use, and health care, and being a POH saliva testing device for POH saliva testing may include a mounting clip, a saliva sample insert apparatus configured to receive a saliva sample, an urine sample, and a blood sample, a pinhole, a LED board, a battery, a set of sensors, and a processor. The processor may be operable to receive data from an external device associated with the POH saliva testing. Based on the data, the processor may provide a notification to a user and receive a user input. The processor may further perform a command selected based on the user input. The wearable and mobile personal digital device may further include a smartphone-based POH apparatus using a technology for making holograms to collect detailed microscopic images from the saliva sample, the urine sample, the blood sample for digital analysis of a molecular composition of cells and tissues in the saliva sample, the urine sample, and the blood sample. The wearable and mobile personal digital device may further include a smartwatch-based POH apparatus using a technology for making holograms to collect detailed microscopic images from the saliva sample, the urine sample, and the blood sample for digital analysis of a molecular composition of cells and tissues in the saliva sample, the urine sample, and the blood sample. The wearable and mobile personal digital device may further include a smart glasses-based POH apparatus using a technology for making holograms to collect detailed microscopic images from the saliva sample, the urine sample, and the blood sample for digital analysis of a molecular composition of cells and tissues in the saliva sample, the urine sample, and the blood sample.

The wearable and mobile personal digital device may further include a handheld POH device configured to transmit results of a plurality of forms of electrochemical analysis directly to a remote computer using a standard mobile phone. The handheld POH device may be configured to be used to monitor diabetes, detect malaria, and analyze drinking water for environmental pollutants. The a handheld POH device may be configured to be used for saliva testing, urine testing, and blood testing to detect drug usage. The saliva testing, the urine testing, and the blood testing may be performed without a need for collection facilities or same-sex observed collections thereby providing performing the saliva testing, the urine testing, and the blood testing immediately after accidents. The POH saliva testing may include POH saliva mouth swab drug tests to detect drugs in a user immediately after use and for one or more days afterwards. The POH saliva testing may be used for pre-employment drug testing, random drug testing, and post-accident drug testing and is a part of a comprehensive drug testing program. The POH saliva testing may be used to detect abuse of common illicit drugs including marijuana, cocaine, heroin, illicit drugs, and prescription drugs. The saliva testing, the urine testing, and the blood testing may include testing for HIV to find lentivirus being a subgroup of retrovirus that causes a HIV infection and AIDS. The HIV infects vital cells in a human immune system including helper T cells including $CD4^+$ T cells, macrophages, and dendritic cells. The HIV infection results in lowering levels of the $CD4^+$ T cells through a plurality of mechanisms including pyroptosis of abortively infected T cells, apoptosis of uninfected bystander cells, direct viral killing of infected cells, and killing of infected $CD4^+$ T cells by CD8 cytotoxic lymphocytes that recognize infected $CD4^+$ T cells.

In an example embodiment, the wearable and mobile personal digital device may be further configured to implement artificial intelligence financial and personal health data processing, multimedia capture, payment transactions, and digital global POH data processing for mobile and wearable devices. More specifically, the processor may be further configured to receive a first input of a user and, in response to the first input of the user, initiate one or more sensors to capture multimedia to obtain captured multimedia. The processor may receive a second input of the user. The first input of the user may include a touch engagement of the user with a display of a mobile and wearable device and the second input of the user includes a touch release of the user from the display of the mobile and wearable device. The processor may analyze data associated with the first input of the user and the second input of the user. The analyzing may include determining time between the first input of the user and the second input of the user. The processor may, based on the analysis, selectively select a multimedia capture mode or a payment transaction mode. The multimedia capture mode may include the user using the mobile and wearable device to capture multimedia content. The selection of the multimedia capture mode and the transaction mode is determined by comparison of the time between the first input and the second input with a predetermined time. Only a multimedia storing mode or a transaction mode can be selected at a single time. The multimedia capture mode may be associated with a plurality of types of multimedia. Each of the plurality of types of multimedia being captured may be determined by the time between the first input and second input in the multimedia capture mode.

Based on the analysis, the processor may selectively select one of multimedia storing modes or a payment transaction mode. Each of the multimedia storing modes is associated with at least one of a plurality of types of the multimedia. In response to the selection of the multimedia capture storing modes, the processor may process the captured multimedia to obtain a type of the multimedia captured in the multimedia capture mode. The processor may store the type of the multimedia captured and the captured multimedia to a database to obtain a stored type of the multimedia. In response to the selection of the payment transaction mode, the processor may receive transaction data. The transaction data may include at least a payment amount and a recipient. Based on the transaction data, user payment data, and recipient payment data, the processor may perform a payment transaction. The user payment data and the recipient payment data may be stored in the database.

The mobile and wearable device may include at least one of a handheld computing device, a smartphone, a tablet computer, a personal digital assistant, a e-textile item, an activity tracker, a smartwatch, smartglasses, a Global Positioning System (GPS) watch, a mixed reality device, a computer-mediated reality device, a clothing technology device, and a wearable device, the wearable device having a band adapted to secure the wearable device on a human body, the human body including a wrist, an arm, a neck, a head, a leg, a waist, an ear, a finger, and any other part of the human body. The band may be adapted to secure the wearable device under, within or on clothing. The band may include a rechargeable battery configured to power the wearable device.

The processor may further be configured to use a global world universal digital mobile and wearable currency. The processor may receive a transfer request. The transfer request may be authorized upon receiving authorization data from a sender having a sender account from which funds are transferred from. The authorization data may include a password, personal identification number (PIN) code, and biometric data comprising a face of the sender. Based on the receiving, the processor may authorize the sender to provide the transfer request when the authorization data providing for the transfer request matches previously registered corresponding authorization data. The transfer may be associated with an amount represented in tokens of the global world universal digital mobile and wearable currency stored on the mobile and wearable device of the sender. The transfer request may include at least the sender account, a recipient account, and the amount. Based on the transfer request, prior to transferring, the processor may encrypt the currency by assigning a unique key to the transferring and signing the global world universal digital mobile and wearable currency using a cryptographic signature the amount from the sender account to the recipient account. The tokens stored on the mobile and wearable device of the sender are printed with a face of the sender. Upon transfer from the mobile and wearable device of the sender to a mobile and wearable device of the recipient, the tokens are converted by replacing the senders face with the recipient face. The currency is not a currency of any national government but is operable to be exchanged by the mobile device into a user defined national currency.

In an example embodiment, the POH saliva testing may include POH molecular diagnostics to analyze biological markers in a genome and proteome by applying molecular biology to medical testing. Body fluids are used to diagnose and monitor diseases, detect a risk, and decide therapies to work for patients. The POH saliva testing of the body fluids includes analyzing specifics of the patients and diseases, including infectious diseases, oncology, a human leucocyte antigen, coagulation, and pharmacogenomics.

The POH saliva testing may include POH screening using a group of sensors. The POH screening is used in a population to identify a possible presence of an as-yet-undiagnosed disease in the individuals without disease signs or symptoms. The individuals may include a pre-symptomatic or unrecognized symptomatic disease. The POH screening is used in screening interventions to identify diseases in early stages and to enable early disease intervention and management to reduce mortality and suffering from a disease. The POH screening may include: a universal screening including screening of a plurality of individuals in a specific category, a case finding including screening a group of individuals based on a presence of risk factors. The POH screening tests of the POH screening include one or more of the following: a cancer screening including a pap smear or liquid-based cytology to detect potentially precancerous lesions and prevent cervical cancer, Mammography to detect breast cancer, colonoscopy and fecal occult blood test to detect colorectal cancer, dermatological check to detect melanoma; a purified protein derivative test to screen for exposure to tuberculosis; beck depression inventory to screen for depression; Social Phobia and Anxiety Inventory Brief (SPAI-B), the Liebowitz Social Anxiety Scale and social phobia inventory to screen for social anxiety disorder; alpha-fetoprotein, blood tests and ultrasound scans for pregnant women to detect fetal abnormalities; bitewing radiographs to screen for interproximal dental caries; ophthalmoscopy or digital photography and image grading for diabetic retinopathy; ultrasound scan for abdominal aortic aneurysm; screening of potential sperm bank donors; screening for metabolic syndrome; and screening for potential hearing loss in newborns.

In an example embodiment, the POH saliva testing device is a slide-on attachment for the AI wearable and mobile personal digital device of the user that has the camera with a polarized light and magnification to take close-up and super clear images of skin lesions. The slide-on attachment works in conjunction with a mobile application to enable the user to take an image. The camera has a polarised light that goes into the skin to show the skin lesions, the camera has at least 20-fold magnification capacity. The mobile application enables the user to mark the skin legion on a virtual body and to send the virtual body with the skin legion to a health professional for a feedback. Sending the virtual body includes charging a fee.

In an example embodiment, the POH saliva testing device is used by the user recovering from skin cancer who has to see the health professional on a regular basis. The user having the POH saliva testing device keeps track of skin lesions, monitors changes in the skin lesions, and shares images of the skin lesions with the health professional without having to come in for an appointment to the health professional. In case the health professional has a concern associated with the images, the user schedules a follow up appointment with the health professional.

In an example embodiment, the POH saliva testing device is an optical probe for a real-time diagnosis of epithelial-based types of cancer to identify and classify precancerous and cancerous skin lesions at an early. The identifying is performed in 80-95 seconds. The optical probe uses both imaging and non-imaging optics to penetrate a cervix to reach a stroma and create a map indicating an exact location and classification of a diseased skin lesion.

In an example embodiment, the POH saliva testing device is a user-agnostic, highly correlated tool used to eliminate a need for biopsies and create an optimized environment for cancer and pre-cancer diagnoses.

In an example embodiment, the POH saliva testing device is used to diagnose other HPV-related types of cancer that develop in epithelium cells including oral cancer, laryngeal cancer, and colon cancer.

In an example embodiment, the POH saliva testing device is a Health Insurance Portability and Accountability Act-compliant skin cancer screening platform for a mobile and cloud-based data processing machine learning and artificial intelligence apparatus that enables the health professional to identify and monitor changes in skin of the user. The mobile and cloud-based data processing machine learning and artificial intelligence apparatus supports the Total Body Photography method that uses at least 18 poses that cover a body of the user using an SLR camera or a smartphone.

In an example embodiment, the POH saliva testing device is associated with an algorithm based on a concept of aerial photos to allow the health professional to identify a mole, take measurements associated with the mole, track parameter changes associated with the mole, and compare the measurements over time.

In an example embodiment, the POH saliva testing device is associated with early-stage breast cancer screening by placing the POH saliva testing device against a breast of the user, obtaining a 3-dimensional image of a breast tissue in 6 seconds, and identifying early-stage malignant growths on the 3-dimensional image;

In an example embodiment, the POH saliva testing device is associated with using radio frequency technology being safe and non-ionizing to allow self-screenings to be used instead of X-ray-based painful and uncomfortable mammograms. The POH saliva testing device is associated with using image processing algorithms to diagnose and monitor medical conditions of the user. The POH saliva testing device is associated with using sensors and enhanced computing ability provided by the processor or an external device to provide a practical, accurate, and low-cost solution for medical diagnosis and monitoring.

The sensors include image sensors that capture photos and videos with significant detail and resolution of at least 10 megapixels to enable analysis of the photos and the videos for self-diagnosis of a disease, self-monitoring of health conditions of the user using the AI wearable and mobile personal digital device.

Thus, various AI wearable and mobile personal digital devices for facilitating mobile device payments, personal saliva testing, personal use, and health care, and being POH saliva testing devices for POH saliva testing have been described. Although embodiments have been described with reference to specific example embodiments, it will be evident that various modifications and changes may be made to these embodiments without departing from the broader spirit and scope of the system and method described herein. Accordingly, the specification and drawings are to be regarded in an illustrative rather than a restrictive sense.

What is claimed is:

1. An artificial intelligence (AI) wearable and mobile personal digital system for facilitating mobile device payments, personal saliva testing, personal use, and health care, and being a point of healthcare (POH) saliva testing device for POH saliva testing, the AI wearable and mobile personal digital system comprising a mobile device physically connected with a portable saliva testing device, the portable saliva testing device comprising:

a mounting clip connecting the portable saliva testing device to the mobile device in front of a camera of the mobile device;

a saliva sample insert apparatus, wherein the saliva sample insert apparatus is configured to receive a saliva sample;

a pinhole;

a light-emitting diode (LED) board;

a battery; and a set of sensors, wherein the set of sensors includes at least a biosensor including a thin-film silicon photonic biosensor, the biosensor including at least a film made of nanoparticles and polymers, wherein the biosensor uses beams of light to detect changes in a composition of the saliva sample of the user placed on the film, each of the saliva sample comprising a biological entity including one or more of a protein, a deoxyribonucleic acid (DNA), and a ribonucleic acid (RNA);

wherein the mobile device comprises:

a processor being operable to:

receive data from an external device associated with POH saliva testing, the external device including a digital device associated with one or more of a health care center, a hospital, an emergency center, a saliva research center, and a deoxyribonucleic acid genetic testing and analysis authority;

based on the data, provide a notification to a user;

receive a user input;

perform a command, the command being selected based on the user input;

provide a natural language user interface to communicate with the user, the natural language user interface being operable to sense a user voice and provide a response in a natural language to the user;

a near field communication (NFC) unit communicatively coupled to the processor;

a display communicatively coupled to the processor, the display including a touchscreen, wherein the display includes a force sensor, wherein the force sensor is operable to sense a touch force applied by the user to the display and calculate coordinates of a touch by the user, and further operable to analyze the touch force and, based on the touch force, select a tap command or a press command based on a predetermined criteria, wherein each of the tap command and the press command is executed based on a duration of the touch of the user using one or more applications running on the mobile device;

a projector communicatively coupled to the processor, the projector being operable to project a data onto an arm of the user, the data including a virtual keyboard operable to provide inputs to the processor and one or more of the following: the notification, time data, data requested by the user, a caller name, a text message, a reminder, a social media alert, an email, and a weather alert;

a timepiece unit communicatively coupled to the processor and configured to provide the time data;

one or more activity tracking sensors communicatively coupled to the processor to track activity of the user, wherein the one or more activity tracking sensors are operable to track snoring and, based on tracking of the snoring, produce an alarm to break snoring;

a memory unit communicatively coupled to the processor;

a communication circuit communicatively coupled to the processor and operable to connect to a wireless network and communicate with the external device;

a housing adapted to enclose at least the processor, the display, the one or more activity tracking sensors, the memory unit, and the communication circuit;

an input unit communicatively coupled to the processor, wherein the input unit extends from the housing and is configured to perform one or more of a rotational motion and a linear motion, wherein the user provides commands to the processor by moving the input unit; and a band adapted to attach to the housing and to secure the mobile device on a user body, wherein the mobile device comprises a wristwatch;

biometric sensors disposed within the band and operable to sense one or more biometric parameters of the user, wherein based on detection that the one or more of the biometric parameters exceed predetermined limits, the biometric sensors are configured to produce the alarm, wherein the biometric sensors include lenses operable to use infrared LEDs and visible-light LEDs to sense a heart rate of the user, wherein the biometric sensors include a skin contact sensor data engine, the skin contact sensor data engine being operable to monitor an electrocardiogram of the user and the heart rate of the user, the electrocardiogram and the heart rate being identification and personal data of the user, wherein the skin contact sensor data engine is operable to prompt the user to enter a personal identification number and the processor is operable to associate the personal identification number with both the electrocardiogram and the heart rate obtained after the mobile device has been secured to a wrist of the user, wherein processor stores the electrocardiogram and the heart rate in the memory unit as a reference electrocardiogram and a reference heart rate; and an adhesive sensor system wearable on a skin of the user body, consisting of a tri-axial accelerometer, a microcontroller, and a Bluetooth Low Energy transceiver, the adhesive sensor system being operable to detect falls of the user based on data provided by the tri-axial accelerometer;

a thermal infrared (IR) sensor worn on the skin of the user body and operable to sense a radiation having a range of wavelengths from 800 nanometer to hundreds of micrometers emitted by the user body;

a haptic touch control actuator operable to produce a haptic feedback in response to one or more events, the one or more events including receiving of the alert, receiving of a notification, a confirmation, movement of the mobile device, receiving of the user input, and sensing of the one or more biometric parameters, the haptic feedback being sensed by the user body, wherein the haptic feedback includes a plurality of feedback types, each of the one or more events being associated with one of the plurality of feedback types, the plurality of feedback types including at least one-time vibration and two-times vibration;

a further battery disposed in the housing;

a magnetic inductive charging unit being operable to magnetically connect to the housing and wirelessly connect to the further battery, wherein the magnetic inductive charging unit is operable to wirelessly transfer energy to the further battery, wherein the magnetic inductive charging unit is integrated into the housing;

wherein the user input is received using one or more of the display, the input unit, and the natural language user interface;

wherein the mobile device further comprises the camera communicatively coupled to the processor and operable to:

capture an image of the saliva sample inserted into the saliva sample insert apparatus, the image being processed by the processor by analyzing the changes in the composition of the saliva sample, wherein the detecting the changes includes determining a level of binding between a DNA probe and a target microRNA to figure out a level of the target microRNA in the saliva sample, wherein the level of the target microRNA is indicative of a presence of types of cancer, cardiac disease, and health issues; and capture an optical code of a product for sale by a merchant, the optical code including one or more of the following: a linear dimensional barcode, a two-dimensional barcode, a snap tag code, and a Quick Response (QR) code;

wherein the processor is further operable to read the optical code to obtain one or more of a product information and a merchant information encoded in the optical code and, based on the merchant information, perform a payment transaction, wherein the processor is configured to perform the payment transaction by sending payment data by the NFC unit to a merchant NFC unit of the merchant;

a swipe card reader communicatively coupled to the processor and operable to read data of a payment card swiped through the swipe card reader, the data being transmitted to the processor or the external device; and wherein the processor of the mobile device is further operable to:

generate, based on user payment data and user personal data, a unique code encoding the user payment data and the user personal data, the user payment data and the user personal data being stored in the memory unit;

prompt the user to touch the display to scan user fingerprints;

determine the heart rate and the electrocardiogram of the user using the biometric sensors to obtain determined heart rate and determined electrocardiogram;

compare the scanned user fingerprints, the determined heart rate and the determined electrocardiogram with reference fingerprints stored in the memory unit, reference heart rate, and reference electrocardiogram;

detect matches of the scanned user fingerprints with the reference fingerprints, the determined heart rate with the reference heart rate, and the determined electrocardiogram with the reference electrocardiogram; and wherein the processor is configured to provide, after the detecting of the matches, a unique code via the display to a merchant digital device associated with one or more of a healthcare center, a hospital, an emergency center, and a saliva research center, wherein the merchant device reads the code for performing the payment transaction; and wherein the processor, upon performing the payment transaction, is configured to provide a payment confirmation to the user, the payment confirmation being provided using the haptic feedback; and wherein the display is further configured to display data associated with the activity of the user detected by the activity sensors, the detected activity of the user including calories burned, sleep quality, breaths per minute, snoring breaks, steps walked, and distance walked.

2. The system of claim 1, wherein the camera is further operable to:
track a face, fingers, gestures, and other biometric personal data; and
the processor is further operable to:
analyze the face, the fingers, the gestures, and the other biometric personal data tracked by the camera;
analyze saliva data obtained from the saliva sample insert apparatus;
recognize speech; and
subtract a background noise from the speech.

3. The system of claim 1, wherein the camera is further operable to perform an optical character recognition of a data, the data including one or more of the following: a typewritten text, a printed text, and an image, the data being scanned from a document, the document including one or more of the following: a passport, an invoice, a bank statement, a computerized receipt, a business card, a mail, a printout of static-data, a book, and a print publication.

4. The system of claim 1, wherein the display is operable to be activated based on one or more of the following: a movement of a user hand, a movement of the user body, a gesture performed by the user in proximity to the display, and a user voice.

5. The system of claim 1, wherein the communication circuit includes one or more of the following: a wireless transceiver, a Bluetooth module, a Wi-Fi module, and a communication port, wherein the communication port includes one or more of the following: a universal serial bus port, a parallel port, an infrared transceiver port, and a radiofrequency transceiver port.

6. The system of claim 1, further comprising:
a microphone operable to:
sense voice data, the voice data being obtained from the user and including a voice command, a voice memo, or a voice message; and
transmit the voice data to the processor; and
a light indicator being operable to show a light indication in response to receiving the data from the external device, wherein upon a predetermined movement of the user body the light indication stops showing the light indication and initiates the display to display the data received from the external device.

7. The system of claim 6, wherein the processor is further operable to:
recognize the voice data to obtain a user request;
transmit the user request to the external device, wherein a plurality of applications running on the external device are visualized on the display using a form factor;

transmit the user request to one or more of the external device, the healthcare center, the hospital, the emergency center, the saliva research center, and deoxyribonucleic acid (DNA) genetic testing and analysis authorities.

8. The system of claim 1, wherein the POH saliva testing includes a diagnostic technique that involves an analysis of a saliva of the user to identify markers of one or more of endocrine, immunologic, inflammatory, infectious, and health conditions,
  wherein the POH saliva testing uses a biological fluid for assaying steroid hormones including cortisol, a genetic material including ribonucleic acid (RNA), proteins including enzymes and antibodies, and a plurality of substances including natural metabolites, a saliva nitrite, a biomarker for a nitric oxide status, a Cardiovascular Disease, a Nitric Oxide, a salivary biomarker for cardio-protection,
  wherein the POH saliva testing is used to screen for and diagnose a plurality of health conditions and disease states including Cushing's disease, anovulation, HIV, cancer, parasites, hypogonadism, and allergies;
  wherein the POH saliva testing is used to assess circadian rhythm shifts in astronauts before flight and to evaluate hormonal profiles of soldiers undergoing military survival training;
  wherein the POH saliva testing is performed as a POH saliva testing cite to provide collection, safety, non-invasiveness, affordability, accuracy, and capacity to circumvent venipuncture as compared to blood testing and a plurality of types of diagnostic testing;
  wherein upon obtaining multiple saliva samples, the POH saliva testing is used to perform chronobiological assessments spanning hours, days, or weeks;
  wherein collecting a whole saliva by passive drool during the POH saliva testing facilitates increasing a size of sample collection to allow the saliva samples to be tested for a plurality of biomarkers, freezing a left over specimen of the saliva sample of the saliva samples to be further used, to eliminate contamination by eliminating extra saliva collection devices and a need to induce a saliva flow;
  wherein the POH saliva testing provides for detection of steroid hormones and antibodies in the saliva sample, additional proteins, a genetic material, and markers of nutritional status.

9. The system of claim 1, wherein the POH saliva testing includes testing saliva components using a glucose test or a cholesterol test, the glucose test and the cholesterol test being grouped together into a POH saliva panel;
  wherein the POH saliva testing is used in health care to determine physiological and biochemical states including a disease, a mineral content, pharmaceutical drug effectiveness, and organ function of the user, and to detect drug abuse in drug tests;
  wherein the POH saliva panel includes a basic metabolic panel or a complete saliva count, wherein the basic metabolic panel measures sodium, potassium, chloride, bicarbonate, blood urea nitrogen (BUN), magnesium, creatinine, glucose, and calcium; and
  wherein the POH saliva testing includes tests on cholesterol levels to determine a total cholesterol level, a low-density lipoprotein (LDL) cholesterol level, a high-density lipoprotein (HDL) cholesterol level, and a triglyceride level.

10. The system of claim 9, wherein the POH saliva testing is associated with salivary glands of a human including parotid glands, submandibular glands, sublingual glands, and minor salivary glands, wherein the salivary glands and the minor salivary glands secrete a mixture of salivary components including biological chemicals, electrolytes, proteins, genetic material, and polysaccharides; wherein the mixture of salivary components enters an acinus and duct system of the salivary gland from surrounding capillaries via an intervening tissue fluid, wherein a plurality of substances are produced within the salivary glands; wherein a level of each of the salivary components varies depending on a health status of the user and a presence of a disease; wherein measuring the salivary components in the saliva is used to screen for infections, allergies, hormonal disturbances, and neoplasms.

11. The device of claim 1, further comprising a vibration unit in communication with the processor, the vibration unit being activated in response to receiving the data from the external device to notify the user about receipt of the data;
  wherein the notification is provided via one or more of the following: a vibration, a sound, and a light indication.

12. The system of claim 1, wherein the POH saliva testing includes detecting conditions including one or more of the following: a Cushing's disease; an Addison's disease, altered female hormone states including polycystic ovary syndrome, menopause, anovulation, and hormonal alterations in cycling women; altered male hormone states including hypogonadism, andropause, and hyperestrogenicstates; metabolic disturbances including insulin resistance, diabetes, and metabolic syndrome; benign and metastatic neoplasms including breast cancer, pancreatic cancer, and oral cancer; infectious conditions including HIV, viral hepatitis, amoebiasis, and *helicobacter pylori* infection; and allergic conditions including food allergy.

13. The system of claim 1, wherein the processor is further operable to:
  detect absence of interaction of the user with the display, wherein the detection is made based on an eye tracking of the user, a head tracking of the user, and a spatial position of the housing;
  based on the detecting, dim the display; and
  activate the display based on the spatial position of the housing or a gesture of the user body.

14. The system of claim 1, wherein the POH saliva testing includes a personal genome testing to provide a health and carrier status for users having a genetic disease, wherein the POH saliva testing is used to test for a genetic carrier disease including Bloom Syndrome; a recessive gene disorder associated with height disorders and a predisposition to develop cancer;
  wherein the POH saliva testing is used to test the user for one or more diseases selected from the following: a Parkinson's disease, a nervous system disorder impacting movement, a Late-onset Alzheimer's disease, a progressive brain disorder destroying memory and thinking skills, a Celiac disease, a disorder resulting in inability to digest gluten, an Alpha-1 antitrypsin deficiency, a disorder that raises a risk of lung and liver disease, early-onset primary dystonia, a movement disorder involving involuntary muscle contractions and uncontrolled movements, factor XI deficiency, a blood-clotting disorder, Gaucher disease type 1, an organ and tissue disorder, Glucose-6-Phosphate Dehydrogenase (G6PD) deficiency, a red blood cell condition, hereditary hemochromatosis, an iron overload disorder, hereditary thrombophilia, and a blood-clot disorder.

15. The system of claim 1, wherein the POH saliva testing is used in clinical and experimental psychological settings to investigate psychological phenomenon including anxiety, depression, a posttraumatic stress disorder, and behavioral disorders;
> wherein the POH saliva testing is used to test a cortisol level and an alpha amylase level being indicative of a stress level, wherein the cortisol level correlates with the stress level, wherein the cortisol level rises slowly over time and takes time to return to a base level thereby indicating that cortisol is associated with a chronic stress level;
>
> wherein the alpha amylase level spikes when confronted with a stressor and returns to base level after the stress thereby making measurement of the alpha amylase level to be a psychological research studying acute stress responses;
>
> wherein saliva samples to test the cortisol level and the alpha amylase level are collected from users by having the users drool through a straw into a collection tube while experiencing a stimulus, wherein the saliva samples are taken at a predetermined interval to record a gradual change in the cortisol level and the alpha amylase level, wherein the collecting of saliva samples is non-invasive;
>
> wherein the cortisol level corresponds to experiencing physiological symptoms of nervousness by the users including a heart rate, sweating, and skin conductance;
>
> wherein the testing of the alpha amylase level in the saliva samples provides examining sympathoadrenal medullary (SAM) activity; wherein the alpha amylase level correlates with autonomic nervous system activity levels and reacts to a hormone being norepinephrine.

16. The system of claim 1, wherein the processor is further operable to:
- analyze a message received by the external device, the analyzing including one or more of the following: parsing a text; reading an image, and recognizing a voice;
- based on the analyzing, display one or more possible replies;
- receive, from the user, a selection of a reply from the one or more possible replies; and
- based on the selection, send the reply to the external device associated with one of the healthcare center, the hospital, the emergency center, the saliva research center and DNA Genetic Testing and Analysis authorities.

17. The system of claim 1,
wherein the system is used as a POH see-through screening apparatus, and
wherein the portable saliva testing device comprises a camera with a polarized light and magnification to take close-up and super clear images of skin lesions, wherein the portable saliva testing device works in conjunction with a mobile application running on the processor to enable the user to take an image, wherein the camera has a polarized light that goes into the skin to show the skin lesions, the camera has at least 20-fold magnification capacity, the mobile application enabling the user to mark the skin legion on a virtual body and to send the virtual body with the skin legion to a health professional for a feedback, wherein sending the virtual body includes charging a fee;
wherein the system is used by the user recovering from skin cancer who has to see the health professional on a regular basis;
wherein the user of the system keeps track of skin lesions, monitors changes in the skin lesions, and shares images of the skin lesions with the health professional without having to come in for an appointment to the health professional, wherein in case the health professional has a concern associated with the images, the user schedules a follow up appointment with the health professional;
wherein the POH saliva testing is associated with an optical probe for a real-time diagnosis of epithelial-based types of cancer to identify and classify precancerous and cancerous skin lesions at an early, wherein the identifying is performed in 80-95 seconds, wherein the optical probe uses both imaging and non-imaging optics to penetrate a cervix to reach a stroma and create a map indicating an exact location and classification of a diseased skin lesion;
wherein the POH saliva testing is a user-agnostic, highly correlated tool used to eliminate a need for biopsies and create an optimized environment for cancer and precancer diagnoses;
wherein the POH saliva testing is used to diagnose other HPV-related types of cancer that develop in epithelium cells including oral cancer, laryngeal cancer, and colon cancer.

18. The system of claim 1,
wherein the processor is further operable to:
- control an operation of a camera of the external device;
- access audio files stored on the external device;
- wirelessly connect with earphones; and
- reproduce the audio files using the earphones;

wherein the POH saliva testing is associated with a Health Insurance Portability and Accountability Act-compliant skin cancer screening platform for a mobile and cloud-based data processing machine learning and artificial intelligence apparatus configured to enable a health professional to identify and monitor changes in skin of the user, the mobile and cloud-based data processing machine learning and artificial intelligence apparatus supports a Total Body Photography method, the Total Body Photography method uses at least 18 poses that cover a body of the user using a single-lens reflex (SLR) camera or a smartphone;
wherein the POH saliva testing is associated with using an algorithm based on a concept of aerial photos to allow the health professional to identify a mole, take measurements associated with the mole, track parameter changes associated with the mole, and compare the measurements over time;
wherein the POH saliva testing is associated with using radio frequency technology being safe and non-ionizing to allow self-screenings to be used instead of X-ray-based painful and uncomfortable mammograms, wherein the POH saliva testing is associated with using image processing algorithms to diagnose and monitor medical conditions of the user, wherein the POH saliva testing is associated with using sensors and enhanced computing ability provided by the processor or the external device for medical diagnosis and monitoring;
wherein the sensors include image sensors that capture photos and videos with resolution of at least 10 megapixels to enable analysis of the photos and the videos for self-diagnosis of a disease, self-monitoring of health conditions of the user using the AI wearable and mobile personal digital device.

19. The system of claim 18, wherein the processor is configured to perform a payment transaction, the payment transaction being performed by the processor is associated with a NFC, the payment transaction being performed for purchases online and offline, wherein a payment associated with the payment transaction is transferred from a pre-paid account of the user or charged to a mobile account of the user or a bank account of the user;
- wherein the payment includes at least a one-touch and one-scan payment for street parking in demarcated areas, the payment being performed using a license plate, transponder tags, barcode stickers, and reading the code from the display;
- wherein a merchant uses a combination of the NFC and the code on the display for performing the one-touch and one-scan payment;
- wherein the NFC is used to establish radio communication with the external device by touching the housing and the external device or bringing the housing and the external device into proximity, the proximity includes a distance of up to 10 centimeters;
- wherein the processor is operable to operate in three modes, the three modes including an NFC target mode when the mobile device is acting as a credential, a NFC initiator mode when the mobile device is acting as a reader, and an NFC peer-to-peer mode;
- wherein the payment is further associated with advertisement tags, two-dimensional barcodes, and ultra-high frequency tags;
- wherein the processor is operable to be connected to a cloud;
- wherein user credentials are provisioned over an air;
- the payment being associated with a payment application associated with the processor to control transferring of the payment and access payment readers;
- wherein the NFC unit is operable to connect to a third-party NFC device with a server for data;
- wherein the mobile device is adapted to enable a Bluetooth low energy payment;
- wherein the mobile device is associated with one or more of a transactional payment based on Unstructured Supplementary Service Data, Short Message Service, direct operator billing, a credit card mobile payment, an online wallet, a QR code payment, contactless NFC, a cloud-based mobile payment, an audio signal-based payment, a Bluetooth Low Energy signal beacon payment, an in-application payment, a Software Development Kit payment, an Application Programming Interface payment, a social networking payment, and a direct carrier and bank co-operation.

20. The system of claim 18, wherein the POH saliva testing includes human immunodeficiency virus (HIV) testing to find a lentivirus being a subgroup of retrovirus and causing a HIV infection and acquired immunodeficiency syndrome (AIDS), wherein the HIV infection infects vital cells in a human immune system including helper T cells including $CD4^+$ T cells, macrophages, and dendritic cells, wherein the HIV infection results in lowering levels of the $CD4^+$ T cells through a plurality of mechanisms including pyroptosis of abortively infected T cells, apoptosis of uninfected bystander cells, direct viral killing of infected cells, and killing of infected $CD4^+$ T cells by CD8 cytotoxic lymphocytes that recognize infected $CD4^+$ T cells.

21. The system of claim 18, wherein the biometric sensors are further operable to non-invasively monitor a glucose level, the glucose level being monitored using a saliva testing;
- wherein the processor is associated with an operating system operable to pair with third-party applications running on the external device;
- wherein the processor integrates a third-party developer technology and the third-party applications and notifications into a form factor;
- wherein the processor is operable to download applications; and
- wherein the mobile device acts as or is associated with smart textiles, an activity tracker, a smartwatch, smartglasses, a GPS watch, mixed reality, computer-mediated reality, clothing technology, Smart closing, healthcare, augmenter reality, and smart and connected devices.

22. The system of claim 18, wherein the processor is further operable to:
- detect presence of another wearable personal digital device for facilitating mobile device payments, personal use, and health care in proximity to the mobile device for facilitating mobile device payments, personal use, and health care; and
- based on the detecting, initiate data transmission between the mobile device for facilitating mobile device payments, personal use, and health care and the another wearable personal digital device for facilitating mobile device payments, personal use, and health care.

23. The system of claim 18, wherein the processor is further operable to:
- receive, from the user, a content access request for at least one content item of content data stored in the memory unit;
- read access rules stored in the memory unit, the access rules being associated with a use of the at least one content item;
- determine, based on the access rules, that an access to the at least one content item is permitted; and
- reproduce, based on the determining, the at least one content item to the user; wherein the content data includes audio data, video data, text, software, game data; wherein the mobile device acts as a data carrier and includes an interface for sending and receiving data, the memory unit being operable to store received content data, provide payment validation data to the external device, store a record of access made to the stored content data, and the access rules for controlling access to the stored content data; the processor being further operable to access control data and supplementary data including hot links to websites and advertising data; wherein payment data, the stored content data and access rules data are used to reduce a risk of an unauthorized access to the content data.

24. The system of claim 1,
- wherein the system is configured to be one of a smartphone-based POH apparatus, a smartwatch-based POH apparatus, a smart glasses-based POH apparatus, and a handheld POH device,
- wherein the smartphone-based POH apparatus uses a technology for making holograms to collect detailed microscopic images from the saliva sample, the urine sample, and the blood sample for digital analysis of a molecular composition of cells and tissues in the saliva sample, the urine sample, and the blood sample;
- wherein the smartwatch-based POH apparatus uses a technology for making holograms to collect detailed microscopic images from the saliva sample, the urine sample, and the blood sample for digital analysis of a molecular composition of cells and tissues in the saliva sample, the urine sample, and the blood sample;
- wherein the smart glasses-based POH apparatus uses a technology for making holograms to collect detailed microscopic images from the saliva sample, the urine sample, and the blood sample for digital analysis of a molecular composition of cells and tissues in the saliva sample, the urine sample, and the blood sample;

wherein the handheld POH device is configured to transmit results of a plurality of forms of electrochemical analysis directly to a remote computer using a standard mobile phone, wherein the handheld POH device is configured to be used to monitor diabetes, detect malaria, and analyze drinking water for environmental pollutants;

wherein the handheld POH device is configured to be used for saliva testing, urine testing, and blood testing to detect drug usage, wherein the saliva testing, the urine testing, and the blood testing is performed without a need for collection facilities or same-sex observed collections thereby providing performing the saliva testing, the urine testing, and the blood testing immediately after accidents;

wherein the POH saliva testing includes POH saliva mouth swab drug tests to detect drugs in a user immediately after use and for one or more days afterwards; wherein the POH saliva testing is used for pre-employment drug testing, random drug testing, and post-accident drug testing and is a part of a comprehensive drug testing program;

wherein the POH saliva testing is used to detect abuse of common illicit drugs including marijuana, cocaine, heroin, illicit drugs, and prescription drugs;

wherein the saliva testing, the urine testing, and the blood testing include testing for human immunodeficiency virus (HIV) to find lentivirus being a subgroup of retrovirus that causes a HIV infection and acquired immunodeficiency syndrome (AIDS), wherein the HIV infection infects vital cells in a human immune system including helper T cells including $CD4^+$ T cells, macrophages, and dendritic cells, wherein the HIV infection results in lowering levels of the $CD4^+$ T cells through a plurality of mechanisms including pyroptosis of abortively infected T cells, apoptosis of uninfected bystander cells, direct viral killing of infected cells, and killing of infected $CD4^+$ T cells by CD8 cytotoxic lymphocytes that recognize infected $CD4^+$ T cells.

25. The system of claim 24, wherein the processor is further configured to implement artificial intelligence financial and personal health data processing, multimedia capture, payment transactions, and digital global POH data processing for mobile and wearable devices, wherein the processor is further configured to:

receive a first input of a user;

in response to the first input of the user, initiate one or more sensors to capture multimedia to obtain captured multimedia;

receive a second input of the user, wherein the first input of the user includes a touch engagement of the user with a display of the mobile device and the second input of the user includes a touch release of the user from the display of the mobile device;

analyze data associated with the first input of the user and the second input of the user, wherein the analyzing includes determining time between the first input of the user and the second input of the user;

based on the analysis, selectively select a multimedia capture mode or a payment transaction mode, wherein the multimedia capture mode comprises the user using the mobile device to capture multimedia content, wherein the selection of the multimedia capture mode and the transaction mode is determined by comparison of the time between the first input and the second input with a predetermined time, wherein only a multimedia storing mode or a transaction mode to be selected at a single time, and wherein the multimedia capture mode is associated with a plurality of types of multimedia, wherein each of the plurality of types of multimedia being captured are determined by the time between the first input and second input in the multimedia capture mode;

based on the analysis, selectively select one of multimedia storing modes or a payment transaction mode, wherein each of the multimedia storing modes is associated with at least one of a plurality of types of the multimedia;

in response to the selection of the multimedia capture storing modes, process the captured multimedia to obtain a type of the multimedia captured in the multimedia capture mode;

store the type of the multimedia captured and the captured multimedia to a database to obtain a stored type of the multimedia;

in response to the selection of the payment transaction mode, receive transaction data, wherein the transaction data comprises at least a payment amount and a recipient;

based on the transaction data, the user payment data, and recipient payment data, perform a payment transaction, wherein the user payment data and the recipient payment data are stored in the database;

wherein the mobile device includes at least one of a handheld computing device, a smartphone, a tablet computer, a personal digital assistant, a e-textile item, an activity tracker, a smartwatch, smartglasses, a Global Positioning System (GPS) watch, a mixed reality device, a computer-mediated reality device, a clothing technology device, and a wearable device, the wearable device having a band adapted to secure the wearable device on a human body, the human body including a wrist, an arm, a neck, a head, a leg, a waist, an ear, a finger, and any other part of the human body, wherein the band is adapted to secure the wearable device under, within or on clothing, and wherein the band includes a rechargeable battery configured to power the wearable device;

the processor being further configured to use a global world universal digital mobile and wearable currency, the processor being further configured to: receive a transfer request, wherein the transfer request is authorized upon receiving authorization data from a sender having a sender account from which funds are transferred from, the authorization data comprising a password, personal identification number (PIN) code, and biometric data comprising a face of the sender; and based on the receiving, authorize the sender to provide the transfer request when the authorization data providing for the transfer request matches previously registered corresponding authorization data;

wherein the transfer is associated with an amount represented in tokens of the global world universal digital mobile and wearable currency stored on the mobile device of the sender, the transfer request including at least the sender account, a recipient account, and the amount; and based on the transfer request, prior to transferring, encrypt the currency by assigning a unique key to the transferring and signing the global world universal digital mobile and wearable currency using a cryptographic signature the amount from the sender account to the recipient account wherein the tokens stored on the mobile device of the sender are printed with the face of the sender, and upon transfer from the mobile device of the sender to a mobile and wearable device of the recipient, the tokens are converted by replacing the face of the sender with a recipient face, wherein the currency is not a currency of any national government but is operable to be exchanged by the mobile device into a user defined national currency.

26. The system of claim 24, wherein the POH saliva testing includes POH molecular diagnostics to analyze biological markers in a genome and proteome by applying molecular biology to medical testing, wherein body fluids are used to diagnose and monitor diseases, detect a risk, and decide therapies to work for patients;

wherein the POH saliva testing of the body fluids includes analyzing specifics of the patients and diseases, including infectious diseases, oncology, a human leucocyte antigen, coagulation, and pharmacogenomics.

27. The system of claim 24, wherein the POH saliva testing includes POH screening using a group of sensors, wherein the POH screening is used in a population to identify a possible presence of an as-yet-undiagnosed disease in individuals without disease signs or symptoms, the individuals including a pre-symptomatic or unrecognized symptomatic disease;

wherein the POH screening is used in screening interventions to identify diseases in early stages and to enable early disease intervention and management to reduce mortality and suffering from a disease;

wherein the POH screening includes: a universal screening including screening of a plurality of individuals in a specific category, a case finding including screening a group of individuals based on a presence of risk factors, wherein POH screening tests of the POH screening include one or more of the following: a cancer screening including a pap smear or liquid-based cytology to detect potentially precancerous lesions and prevent cervical cancer, Mammography to detect breast cancer, colonoscopy and fecal occult blood test to detect colorectal cancer, dermatological check to detect melanoma; a purified protein derivative test to screen for exposure to tuberculosis; beck depression inventory to screen for depression; Social Phobia and Anxiety Inventory Brief (SPAI-B), a Liebowitz Social Anxiety Scale and social phobia inventory to screen for social anxiety disorder; alpha-fetoprotein, blood tests and ultrasound scans for pregnant women to detect fetal abnormalities; bitewing radiographs to screen for interproximal dental caries; ophthalmoscopy or digital photography and image grading for diabetic retinopathy; ultrasound scan for abdominal aortic aneurysm; screening of potential sperm bank donors; screening for metabolic syndrome; and screening for potential hearing loss in newborns.

\* \* \* \* \*